(12) United States Patent
Lee et al.

(10) Patent No.: US 10,894,086 B2
(45) Date of Patent: Jan. 19, 2021

(54) FUNCTIONAL HYDRATED HYALURONIC ACID AND METHOD FOR PRODUCING COATED LACTIC ACID BACTERIA HAVING EXCELLENT INTESTINAL MUCOADHESIVE ABILITY AND SELECTIVE ANTAGONISTIC ACTION USING SAME

(71) Applicant: ILDONG PHARMACEUTICAL CO., LTD., Seoul (KR)

(72) Inventors: Seung-Hun Lee, Gyeonggi-do (KR); Dae Jung Kang, Gyeonggi-do (KR); Jae-Hoon Kang, Seoul (KR)

(73) Assignee: ILDONG PHARMACEUTICAL CO., LTD., Seoul (KR)

(*) Notice: Subject to any disclaimer, the term of this patent is extended or adjusted under 35 U.S.C. 154(b) by 48 days.

(21) Appl. No.: 15/760,166

(22) PCT Filed: Sep. 19, 2016

(86) PCT No.: PCT/KR2016/010415
§ 371 (c)(1),
(2) Date: Mar. 14, 2018

(87) PCT Pub. No.: WO2017/048098
PCT Pub. Date: Mar. 23, 2017

(65) Prior Publication Data
US 2018/0250412 A1     Sep. 6, 2018

(30) Foreign Application Priority Data
Sep. 14, 2015 (KR) .................. 10-2015-0129986

(51) Int. Cl.
*A61K 35/744*     (2015.01)
*A61K 35/745*     (2015.01)
(Continued)

(52) U.S. Cl.
CPC .............. *A61K 47/36* (2013.01); *A61K 35/74* (2013.01); *A61K 35/744* (2013.01);
(Continued)

(58) Field of Classification Search
CPC ...... A61K 47/36; A61K 35/74; A61K 35/744; A61K 35/745; A61K 35/747; C09D 105/08; C12N 1/20; C08L 5/08; C08L 2203/02
See application file for complete search history.

(56) References Cited

U.S. PATENT DOCUMENTS

2013/0067682 A1* 3/2013 Dong

FOREIGN PATENT DOCUMENTS

KR     10-2007-0104140 A     12/2007
KR     10-2009-0082035        7/2009
(Continued)

OTHER PUBLICATIONS

Office Action corresponding to European Patent Application No. 16846919.5 dated May 4, 2020.
(Continued)

*Primary Examiner* — Marcia S Noble
*Assistant Examiner* — Lauren K Van Buren
(74) *Attorney, Agent, or Firm* — Jenkins, Wilson, Taylor & Hunt, P.A.

(57) ABSTRACT

The present invention relates to a functional hydrated hyaluronic acid and a method for producing 5$^{th}$ generation coated lactic acid bacteria having excellent intestinal mucoadhesive ability and a selective antagonism using the same and, more specifically, to a functional hydrated hyaluronic acid in which components fermented by lactic acid bacteria are captured in hyaluronic acid, which is a natural polymer substance, and a method for producing coated lactic acid bacteria using the same. The quadruply (Continued)

coated lactic acid bacteria coated using the functional hydrated hyaluronic acid according to the present invention is quadruply coated with a water-soluble polymer, a functional hydrated hyaluronic acid, a coating agent having porous particles, and a protein, thereby producing an excellent intestinal mucoadhesive ability, exhibiting an antibacterial action against deleterious bacteria in the intestines, and promoting growth of beneficial bacteria in the intestines.

7 Claims, 14 Drawing Sheets

(51) Int. Cl.

| | | |
|---|---|---|
| A61K 35/747 | (2015.01) | |
| A61K 35/74 | (2015.01) | |
| A61K 47/36 | (2006.01) | |
| A61K 47/10 | (2017.01) | |
| A61K 47/14 | (2017.01) | |
| A61K 47/32 | (2006.01) | |
| A61K 47/38 | (2006.01) | |
| A61K 47/42 | (2017.01) | |
| A61K 9/50 | (2006.01) | |
| C12N 1/20 | (2006.01) | |
| C08B 37/08 | (2006.01) | |
| C08L 5/08 | (2006.01) | |
| C08L 5/00 | (2006.01) | |
| C08L 89/00 | (2006.01) | |
| C08L 93/00 | (2006.01) | |
| C09D 105/08 | (2006.01) | |
| A23L 33/135 | (2016.01) | |
| A23L 5/00 | (2016.01) | |
| A61P 1/00 | (2006.01) | |
| A61P 1/14 | (2006.01) | |
| C07K 14/47 | (2006.01) | |
| C07K 14/415 | (2006.01) | |

(52) U.S. Cl.
CPC .......... *A61K 35/745* (2013.01); *A61K 35/747* (2013.01); *C08L 5/08* (2013.01); *C09D 105/08* (2013.01); *C12N 1/20* (2013.01); *C08L 2203/02* (2013.01)

(56) References Cited

FOREIGN PATENT DOCUMENTS

| KR | 10-2011-0134486 | | 12/2011 |
|---|---|---|---|
| KR | 10-2012-0046676 | | 5/2012 |
| KR | 10-2012-0047792 | | 5/2012 |
| KR | 10-2013-0067682 | | 6/2013 |
| KR | 20130067682 | * | 6/2013 |
| KR | 10-2013-0143229 A | | 12/2013 |
| KR | 101425712 B1 | * | 7/2014 |

OTHER PUBLICATIONS

Chauviere et al. (1992) Competative Exclusion of Diarrheagenic *Escherichia coli* (ETEC) from Human Enterocyte-like Caco-2 Cells by Heat-Killed Lactobacillus. FEMS Microbiology Letters 91:213-218.
Bernet et al. (1993) Adhesion of Human Bifidobacterial Strains to Cultured Human Intestinal Epithelial Cells and Inhibition of Enteropathogen-Cell Interactions. Applied and Environmental Microbiology 59(12): 4121-4128.
Bernet et al. (1994) Lactobacillus acidophilus LA 1 Binds to Cultured Human Intestinal Cell Lines and Inhibits Cell Attachment and Cell Invasion by Enterovirulent Bacteria. Gut 35:483-489.
International Preliminary Report on Patentability corresponding to International Application No. PCT/KR2016/010415 dated Mar. 20, 2018.
International Search Report corresponding to Korean Patent Application Serial No. PCT/KR2016/010415 dated Dec. 21, 2016.
Search Report and Written Opinion corresponding to Brazilian Patent Application No. 112018004949-2 dated Aug. 11, 2020.

* cited by examiner

FIG. 3
A 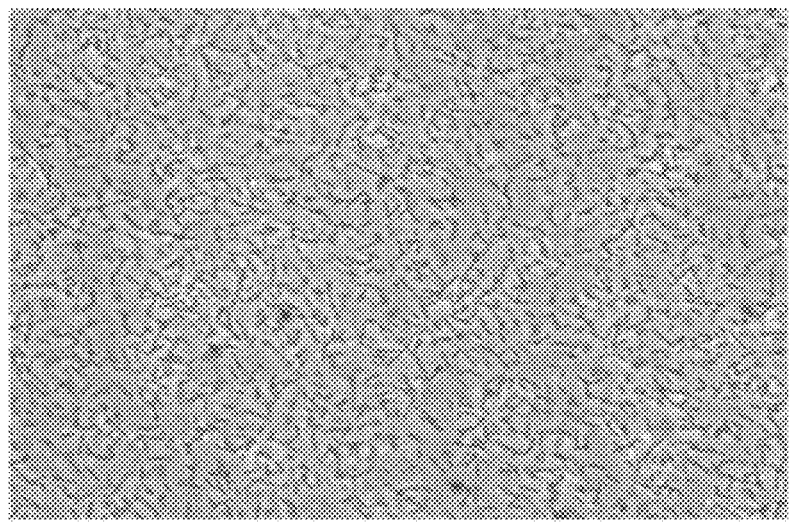
B 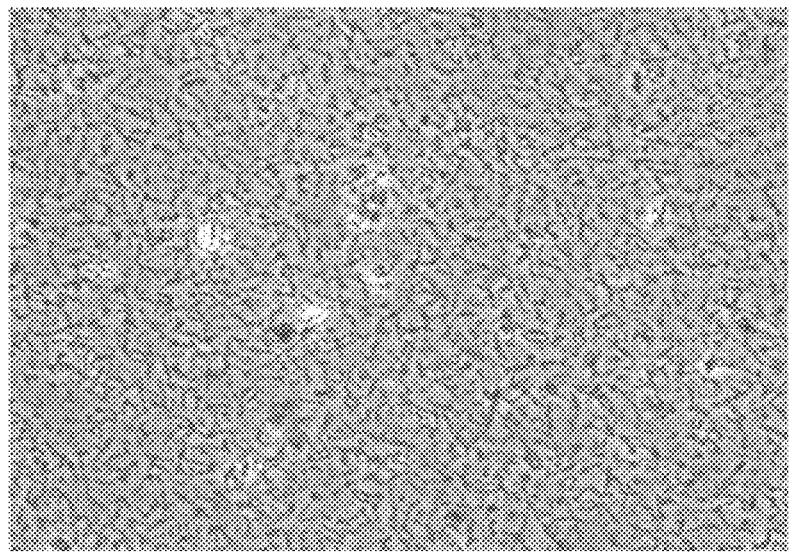

FIG. 4
A 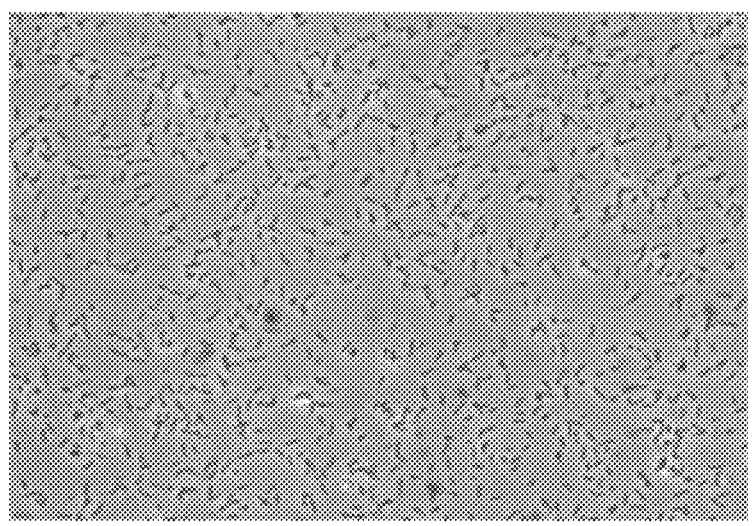
B 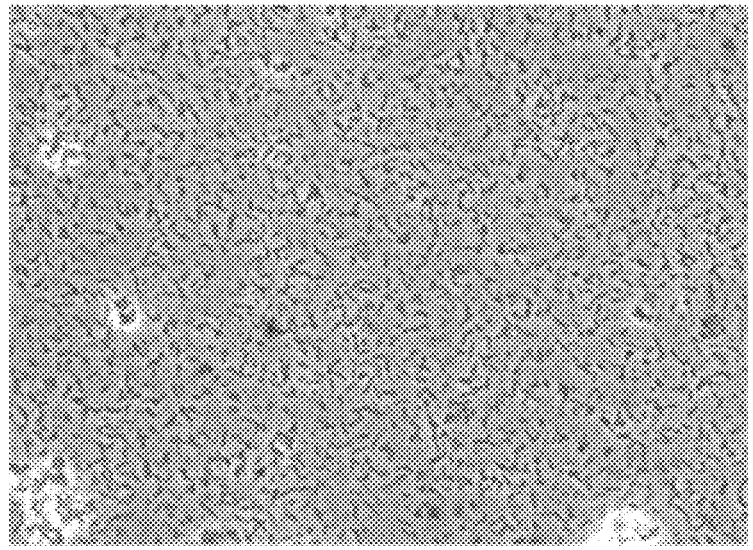

FIG. 5
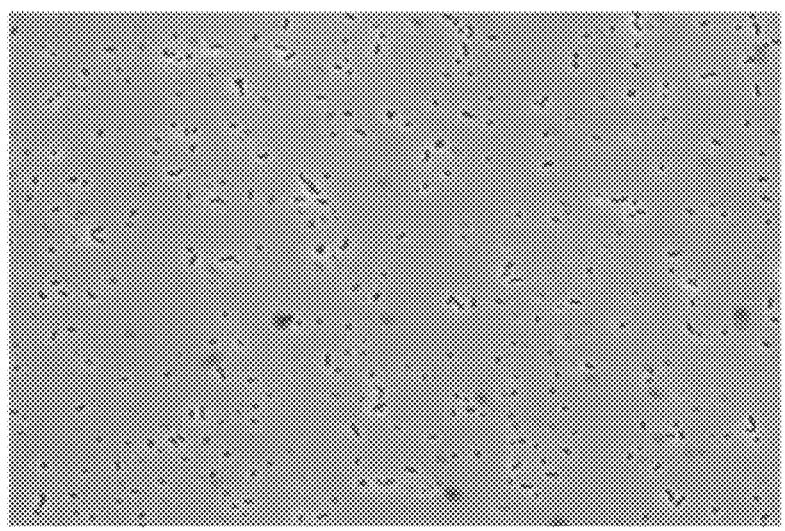
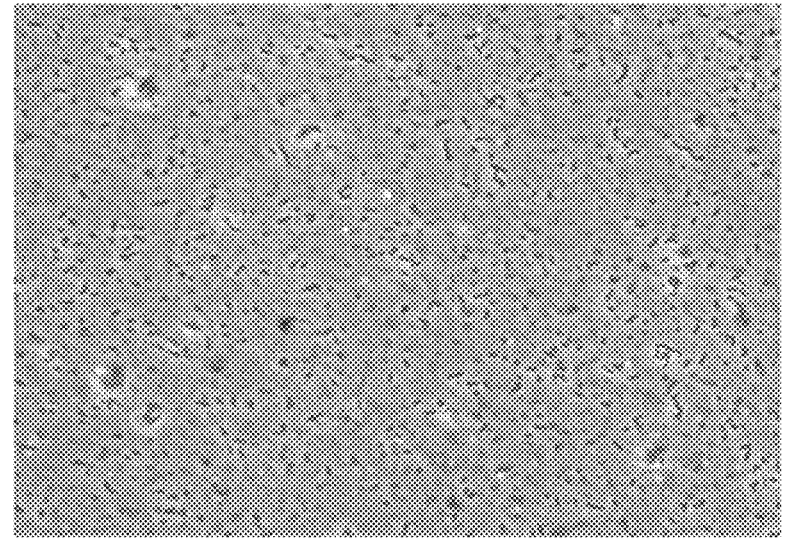

FUNCTIONAL HYDRATED HYALURONIC ACID AND METHOD FOR PRODUCING COATED LACTIC ACID BACTERIA HAVING EXCELLENT INTESTINAL MUCOADHESIVE ABILITY AND SELECTIVE ANTAGONISTIC ACTION USING SAME

TECHNICAL FIELD

The present invention relates to functional hydrated hyaluronic acid and a method for producing coated lactic acid bacteria having excellent intestinal mucoadhesive ability and selective antagonism using same. More particularly, the present invention relates to functional hydrated hyaluronic acid, which is complexed with hyaluronic acid, a natural polymer substance, and a method for producing coated lactic acid bacteria using same. Especially, it relates to a method for producing functional coated lactic acid bacteria which are coated by a water-soluble polymer, a functional hydrated hyaluronic acid, a coating agent having porous particles, and a protein, and has excellent intestinal mucoadhesive ability and selective antagonistic action.

BACKGROUND OF THE INVENTION

The present application claims priority from Korean Patent Application No. 10-2015-0129936, filed on Sep. 14, 2015, the entirety of which is incorporated herein by reference.

More than 400 kinds of microorganisms such as *Bacteroides, Eubacteria, Bifidobacteria* and *Lactobacilli* are inhabited in the intestines of human body. In the intestine of healthy people, beneficial bacteria such as lactic acid bacteria and harmful bacteria have inhabited in the form of microflora. Since the intestinal microflora is disturbed by harmful environment, unhygienic food intake, and taking antibiotics, the lactic acid bacteria decrease and the harmful bacteria such as *Escherichia coli* and *Salmonella* increase.

Probiotics are microbial agents that live in the gastrointestinal tract of humans and animals, and have beneficial effects on humans and animals. The microbial agents include *Lactobacilli, Bifidobacteria,* and *Enterococci.*

The intestinal physiological activity functions of lactic acid bacteria include maintaining the balance of intestinal flora, inhibiting the growth of harmful bacteria, preventing diarrhea, protecting intestinal epithelial cells, inhibiting the absorption of toxic substances, and inhibiting carcinogenesis. In order for *lactobacilli* to act as probiotics, they must bind to the intestinal mucosa and proliferate and have pathological resistance against harmful bacteria.

In order for the lactic acid bacteria to adhere to the intestinal mucosa of the host, they must be adhered to each other by competition with the host strains. Nurmi and Rantala introduced competitive exclusion of harmful microorganisms for the first time and reported that *Salmonella* infection was reduced as a result of inoculation of chicken intestinal contents into freshly hatched chicks. The intestinal microflora of chickens were better adhered to the adsorbed part of the barrier surface cells, produced fatty acids and other antimicrobials, and were reported to be advantageous in competition for nutrients.

Lactic acid bacteria have the property of adsorbing to the intestinal mucosa of the host. It is known that lipoteichoic acid, polysaccharide, and protein, which are components of the cell wall of lactic acid bacteria, are involved in adhesion to the intestinal mucosa. The cell structure of lactic acid bacteria consists of a cell membrane and a cell wall surrounding the cell membrane. The cell walls functionally represent the shape of the lactic acid bacteria and surround the cell membrane to protect the lactic acid bacteria from the external environment. The four major components of the cell wall are peptidoglycan, teichoic acid, S-layer, and polysaccharide, which are involved in binding to the intracellular extracellular matrix. ECM is a stable macromolecular organization that is the basis of epithelial cells and endothelial cells. Lactic acid bacteria bind to dendritic cells (DCs) of the intestinal mucosa, and then transmit various cellular signals including the action of the cells to prevent immune diseases.

When lactic acid bacteria are adhered smoothly to the intestinal mucosa through competitive exclusion, they produce a variety of substances that affect other microorganisms in the intestine. Among them, lactic acid inhibits the survival of other microorganisms by acidifying the intestinal contents.

In general, in order for lactic acid bacteria to enhance an intestinal regulation in the intestines, the ability of the lactic acid bacteria to bind to intestinal mucosa should be better than that of *Escherichia coli* and *Salmonella* to bind to the intestinal mucosa. However, the lactic acid bacteria, which are classified as Gram-positive bacteria are less able to bind to intestinal mucosa than Gram-negative bacteria such as *Escherichia coli* and *Salmonella*. In addition, lactic acid bacteria have different adhesion ability according to the source of separation. The lactic acid bacteria in the genus *Lactobacillus* have relatively good adhesion affinities to the small intestine mucosa, and probiotics of the genus *Bifidobacterium* have excellent adhesion affinities to the large intestine mucosa. In addition, since the plant-derived probiotics have been attached to plant surfaces and evolved symbiotically, the attachment efficiency to the intestinal mucosa of an animal is reduced.

On the other hand, conventional coated techniques for lactic acid bacteria have been classified according to the survival rate when passing through the gastrointestinal tract from the first generation to the fourth generation. The first generation is uncoated lactic acid bacteria, the second generation is enteric coated lactic acid bacteria, the third generation is microencapsulated lactic acid bacteria, and the fourth generation is protein-coated lactic acid bacteria. Thus, these all lactic acid bacteria have been focused on how many lactic acid bacteria reach the gastrointestinal tract when they pass through the gastrointestinal tract with uncoated lactic acid bacteria. In addition, quadruply coated lactic acid bacteria based on the hyaluronic acid referred to as the fifth generation coated technology (see Korean Patent No. 10-1280232) significantly improved the heat tolerance, acid tolerance, and bile tolerance compared with the conventional single or tertiary coated lactic acid bacteria, and contributed greatly to the survival rate of the lactic acid bacteria.

The conventional technology for manufacturing quadruply coated lactic acid bacteria based on hyaluronic acid used hyaluronic acid which is a natural polymer as a coating agent and has remarkably improved heat tolerance, acid tolerance, and bile tolerance compared with conventional single or tertiary coated lactic acid bacteria. However, there are still limitations in the effect of competitive exclusion of intestinal mucosa attachment efficiency, settling time, and gram negative pathogenic strains.

DETAILED DESCRIPTION OF THE INVENTION

Technical Problem

Accordingly, the present inventors have researched to overcome the limitations of conventional coated techniques for lactic acid bacteria and to develop coated techniques for lactic acid bacteria that remarkably improved intestinal mucosa attachment efficiency, intestinal mucosal fixation time, and competitive inhibition effect on intestinal harmful bacteria. As a result, 'functional hydrated hyaluronic acid' in which fermented products of lactic acid bacteria were complexed with (or combined with) hyaluronic acid, a natural polymer substance was developed. The present inventors have accomplished the present invention that the functional hydrated hyaluronic acid can be used as a lactic acid bacterial coating agent exhibiting a desired effect after confirming that it exhibits inhibiting proliferation of harmful bacteria and the promoting proliferation of beneficial bacteria.

Accordingly, another aspect of the present invention is to provide functional hydrated hyaluronic acid complexed with a fermented product of a lactic acid bacteria, wherein the functional hydrated hyaluronic acid complexed with the fermented product of a lactic acid bacteria is prepared by a process comprising: adding hyaluronic acid to a culture medium of a lactic acid bacteria in a ratio of 0.001 to 1 part by weight of hyaluronic acid to 100 parts by weight of a culture medium of a lactic acid bacteria; and dissolving the hyaluronic acid in the culture medium of a lactic acid bacteria upon stirring, followed by concentration under a reduced pressure at 30 to 60° C.

Another aspect of the present invention is to provide lactic acid bacteria coated with the functional hydrated hyaluronic acid.

Another aspect of the present invention is to provide a method for preparing a quadruply coated lactic acid bacteria, the method comprising: (a) conducting a primary coating by mixing a water-soluble polymer with a lactic acid bacteria; (b) conducting a secondary coating by mixing the functional hydrated hyaluronic acid of claim 1 with the primarily coated lactic acid bacteria of step (a); (c) conducting a tertiary coating by mixing a coating agent having porous particles with the secondarily coated lactic acid bacteria of step (b); and (d) conducting a quaternary coating by mixing a protein with the tertiarily coated lactic acid bacteria of step (c).

Another aspect of the present invention is to provide quadruply coated lactic acid bacteria produced by the method for preparing the above-mentioned quadruply coated lactic acid bacteria.

Technical Solution

An embodiment according to an aspect of the present invention provides functional hydrated hyaluronic acid complexed with a fermented product of a lactic acid bacteria, wherein the functional hydrated hyaluronic acid complexed with the fermented product of a lactic acid bacteria is prepared by a process comprising: adding hyaluronic acid to a culture medium of a lactic acid bacteria in a ratio of 0.001 to 1 part by weight of hyaluronic acid to 100 parts by weight of a culture medium of a lactic acid bacteria; and dissolving the hyaluronic acid in the culture medium of a lactic acid bacteria upon stirring, followed by concentration under a reduced pressure at 30 to 60° C.

Another embodiment according to an aspect of the present invention is to provide lactic acid bacteria coated with functional hydrated hyaluronic acid.

Another embodiment according to an aspect of the present invention is to provide a method for preparing a quadruply coated lactic acid bacteria, the method comprising: (a) conducting a primary coating by mixing a water-soluble polymer with a lactic acid bacteria; (b) conducting a secondary coating by mixing the functional hydrated hyaluronic acid of claim 1 with the primarily coated lactic acid bacteria of step (a); (c) conducting a tertiary coating by mixing a coating agent having porous particles with the secondarily coated lactic acid bacteria of step (b); and (d) conducting a quaternary coating by mixing a protein with the tertiarily coated lactic acid bacteria of step (c).

Another embodiment according to an aspect of the present invention provides quadruply coated lactic acid bacteria produced by a method for preparing a quadruply coated lactic acid bacterium.

Hereinafter, the present invention will be described in detail.

The present invention provides functional hydrated hyaluronic acid complexed with a fermented product of a lactic acid bacteria, wherein the functional hydrated hyaluronic acid complexed with the fermented product of a lactic acid bacteria is prepared by a process comprising: adding hyaluronic acid to a culture medium of a lactic acid bacteria in a ratio of 0.001 to 1 part by weight of hyaluronic acid to 100 parts by weight of a culture medium of a lactic acid bacteria; and dissolving the hyaluronic acid in the culture medium of a lactic acid bacteria upon stirring, followed by concentration.

In the present invention, the functional hydrated hyaluronic acid is obtained by combining the culture medium of lactic acid bacteria with hyaluronic acid. It refers to hyaluronic acid complexed with components which exhibit an inhibitory action on the growth of harmful bacteria in the intestines and components which have no effect on the beneficial bacteria or help the growth of the bacteria.

Meanwhile, the present inventors intend to utilize the fermented products of lactic acid bacteria to extract components that do not affect lactic acid bacteria or contribute to the growth of lactic acid bacteria, since representative strains of bacteria classified as beneficial bacteria in intestinal bacterial flora are lactic acid bacteria. Thus the present inventors intend to develop a coating agent exhibiting a desired effect by combining the lactic acid bacterial culture medium with hyaluronic acid.

In other words, functional hydrated hyaluronic acid was prepared by combining adhesion inhibitor against harmful bacteria, such as lipoteichoic acid and peptidoglycan which are representative components contained in the cell structure, and the lactic acid bacterial culture medium which inhibits the growth of harmful bacteria and promotes the growth of beneficial bacteria with hyaluronic acid.

More specifically, the functional hydrated hyaluronic acid in the present invention may be prepared by adding hyaluronic acid in a ratio of 0.001 to 1 part by weight relative to 100 parts by weight of the culture medium of lactic acid bacteria, dissolving it by stirring, and using a method of vacuum evaporation at 30 to 60° C. More preferably, it is prepared by mixing 0.001 to 0.5 part by weight and most preferably 0.001 to 0.25 part by weight, of hyaluronic acid relative to 100 parts by weight of the culture medium of lactic acid bacteria. By the above-mentioned method, the fermented products of lactic acid bacterial are complexed with hyaluronic acid to indicate antimicrobial action against noxious bacteria in the intestines, and indicate promoting proliferation of beneficial bacteria. In particular, the culture medium of lactic acid bacteria obtained by pressurization and tyndallization has adhesion inhibitor for harmful bacteria such as lipoteichoic acid and peptidoglycan which are representative components contained in lactic acid bacteria or its culture medium, and has an effect inhibiting the growth of harmful bacteria and increasing the growth of beneficial bacteria.

Meanwhile, in the present invention, the culture medium of a lactic acid bacteria is prepared by a process comprising the following steps:

(a) heating the culture medium of lactic acid bacteria at 110 to 135° C. for 3 to 7 minutes under pressure;

(b) cooling the pressurized and heated culture medium of step (a) to 25 to 35° C.;

(c) heating the cooled culture medium of step (b) at 105 to 115° C. for 8 to 12 minutes under pressure;

(d) cooling the pressurized and heated culture medium of step (c) to 25 to 35° C.; and (e) heating the cooled culture medium of step (d) at 75 to 85° C. for 20 to 40 minutes, followed by cooling to 25 to 35° C.

The lactic acid bacteria for producing functional hydrated hyaluronic acid are lactic acid bacteria which produce fermented products of an antibacterial component and is at least one and more selected from the groups consisting of *Lactobacillus* sp., *Bifidobacterium* sp., *Streptococcus* sp., *Lactococcus* sp., *Enterococcus* sp., *Pediococcus* sp., *Leuconostoc* sp., *Weissella* sp., Preferably lactic acid bacteria is at least one and more selected from the groups consisting of *Lactobacillus acidophilus* IDCC 3302, *Lactobacillus bulgaricus, Lactobacillus casei, Lactobacillus fermentum, Lactobacillus gasseri, Lactobacillus helveticus, Lactobacillus rhamnosus, Lactobacillus johnsonii, Lactobacillus paracasei, Lactobacillus plantarum, Lactobacillus reuteri, Lactobacillus salivarius, Bifidobacterium bifidum, Bifidobacterium breve, Bifidobacterium infantis, Bifidobacterium lactis, Bifidobacterium longum, Enterococcus faecium, Enterococcus faecalis, Streptococcus faecium, Streptococcus faecalis, Streptococcus thermophilus, Lactococcus lactis* subsp. *lactis, Lactococcus lactis* subsp. *Cremoris, Pediococcus acidolacticii, Pediococcus pentosaceus, Leuconostoc carnosum, Leuconostoc citreum, Leuconostoc gasicomatatum, Leuconostoc gellidum, Leuconostoc inhae, Leuconostoc kimchii, Leuconostoc lactis, Leuconostoc mesenteroides* subsp., *mesenteroides, Leuconostoc paramesenteroides, Weissella cibaria, Weissella confusa, Weissella koreensis, Weissella soli*, and *Weissella viridescens*, more preferably *Lactobacillus acidophilus* IDCC 3302, but is not limited to.

The functional hydrated hyaluronic acid in the culture medium of lactic acid bacteria not only inhibits the adhesion of the intestinal mucosa of *Salmonella typhimurium*, which is regarded as harmful bacteria in the intestines, but also inhibits its growth (Examples 2 and 3).

According to another example of the present invention, in order to evaluate the effect of functional hydrated hyaluronic acid on the growth of beneficial bacteria in the intestines, *Lactobaclliu rhamnosus* represented by *Lactobacillus, Bifidobacterium longum* represented by *Bacillus bifidus*, and *Enterococcus faecium* represented by *Lactococcus lactis* were treated with functional hydrated hyaluronic acid. As a result, proliferation of each microorganism was significantly promoted in the groups treated with functional hydrated hyaluronic acid (Example 4). Meanwhile, according to the example of the present invention, it has been confirmed that conventional hyaluronic acid does not exhibit such an effect of inhibiting harmful bacteria and promoting the proliferation of beneficial bacteria, whereas the functional hydrated hyaluronic acid according to the present invention exhibited such unique functional characteristics by combining lactic acid bacteria fermented products.

As a result of the above-mentioned experimental results, the functionalized hydrated hyaluronic acid can be used as a coating agent for enhancing the proliferation of enteric bacteria in the intestines and exhibiting a selective antagonism to inhibit the growth of harmful bacteria, thereby increasing the adhesion and adhesion time of the intestinal mucosa of lactic acid bacteria.

Accordingly, the present invention provides lactic acid bacteria coated with the functional hydrated hyaluronic acid.

The present invention also provides a method for producing quadruply coated lactic acid bacteria having an excellent adherence of the intestinal mucosa and a selective antagonism using the functional hydrated hyaluronic acid. Specifically, the process for preparing quadruply coated lactic bacteria of the present invention comprises:

(a) conducting a primary coating by mixing a water-soluble polymer with a lactic acid bacteria;

(b) conducting a secondary coating by mixing the functional hydrated hyaluronic acid with the primarily coated lactic acid bacteria of step (a);

(c) conducting a tertiary coating by mixing a coating agent having porous particles with the secondarily coated lactic acid bacteria of step (b); and (d) conducting a quaternary coating by mixing a protein with the tertiarily coated lactic acid bacteria of step (c).

In addition, the process for preparing quadruply coated lactic acid bacteria of the present invention comprises:

(a) conducting a primary coating by mixing a carboxymethyl cellulose (CMC) with a lactic acid bacteria;

(b) conducting a secondary coating by mixing the functional hydrated hyaluronic acid with the primarily coated lactic acid bacteria of step (a);

(c) conducting a tertiary coating by mixing a coating agent having porous particles with the secondarily coated lactic acid bacteria of step (b); and (d) conducting a quaternary coating by mixing a protein with the tertiarily coated lactic acid bacteria of step (c).

In addition, the process for preparing a quadruply coated lactic acid bacterium of the present invention comprises (a) conducting a primary coating by mixing a water-soluble polymer with a lactic acid bacteria;

(b) conducting a secondary coating by mixing the functional hydrated hyaluronic acid with the primarily coated lactic acid bacteria of step (a);

(c) conducting a tertiary coating by mixing a maltodextrin (MD) having porous particles with the secondarily coated lactic acid bacteria of step (b); and (d) conducting a quaternary coating by mixing a protein with the tertiarily coated lactic acid bacteria of step (c).

In addition, the process for preparing quadruply coated lactic acid bacteria of the present invention comprises:

(a) conducting a primary coating by mixing a water-soluble polymer with a lactic acid bacteria;

(b) conducting a secondary coating by mixing the functional hydrated hyaluronic acid with the primarily coated lactic acid bacteria of step (a);

(c) conducting a tertiary coating by mixing a coating agent having porous particles with the secondarily coated lactic acid bacteria of step (b); and (d) conducting a quaternary coating by mixing a whey protein with the tertiarily coated lactic acid bacteria of step (c).

Preferably, the process for preparing a quadruply coated lactic acid bacterium of the present invention comprises:

(a) conducting a primary coating by mixing carboxymethyl cellulose (CMC) with a lactic acid bacteria;

(b) conducting a secondary coating by mixing the functional hydrated hyaluronic acid with the primarily coated lactic acid bacteria of step (a);

(c) conducting a tertiary coating by mixing maltodextrin (MD) having porous particles with the secondarily coated lactic acid bacteria of step (b); and (d) conducting a quaternary coating by mixing whey protein with the tertiarily coated lactic acid bacteria of step (c).

(a) conducting a primary coating by mixing a water-soluble polymer with a lactic acid bacteria:

The water-soluble polymer was selected by evaluating the cross-linking ability with the functional hydrated hyaluronic acid to increase the surface binding strength of lactic acid bacteria. Specifically, a water-soluble polymer, which is used as the cell membrane coating agent and has excellent cross-linking ability of functional hydrated hyaluronic acid of the present invention is not limited thereto, but may be preferably selected from the group consisting of carboxymethylcellulose (CMC), hydroxyethylcellulose (HEC), xanthan gum (XG), guar gum (GG), polyvinylpyrrolidone (PVP), Chitosan, gum arabic, carbopol, sodium alginate, and propylene glycol alginate. It is preferably carboxymethyl cellulose (CMC), hydroxyethylcellulose (HEC), xantha gum (XG), guar gum (GG), polyvinylpyrroridone Chitosan, arabia gum and carbopol, more preferably carboxymethyl cellulose (CMC), polyvinylpyrrolidone (PVP), chitosan, Arabia gum, carbopol, and most preferably carboxymethyl cellulose (CMC).

The primary coating is performed by mixing the water-soluble polymer and at a ratio of 0.1 to 10 parts by weight relative to 100 parts by weight of the lactic acid bacterium culture medium. The mixing ratio of the water-soluble polymer relative to 100 parts by weight of the culture medium of the lactic acid bacteria is, for example, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, and is not limited to the above values if it is within the range of 0.1 to 10 parts by weight relative to 100 parts by weight of the culture medium of lactic acid bacteria.

Preferably, the water-soluble polymer is mixed at a ratio of 0.1 to 5 parts by weight, and most preferably 0.1 to 0.5 part by weight relative to 100 parts by weight of the culture medium of lactic acid bacteria.

Preferably, the primary coating may be performed by mixing carboxymethyl cellulose (CMC) as the water-soluble polymer and a ratio of 0.1 to 10 parts by weighs relative to 100 parts by weight of the culture medium of lactic acid bacteria. Specifically, the mixing ratio of CMC relative to 100 parts by weight of the culture medium of the lactic acid bacteria is, for example, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0 and is not limited to the above values if it is within the range of 0.1 to 10 parts by weight relative to 100 parts by weight of the culture medium of lactic acid bacteria. Preferably, as the water-soluble polymer, CMC is mixed at a ratio of 0.1 to 5 parts by weight, and most preferably 0.1 to 0.5 part by weight relative to 100 parts by weight of the culture medium of lactic acid bacteria.

In the example of the present invention, it was confirmed that carboxymethyl cellulose (CMC) was excellent in cross-linking with functional hydrated hyaluronic acid which is a secondary coating agent (see Table 3).

Therefore, when this base was applied at a concentration of 0.1% (w/v) to 0.4% (w/v), it showed the highest cross-linkinq ability at 0.2% (w/v) (see Table 4).

(b) conducting a secondary coating by mixing the functional hydrated hyaluronic acid with the primarily coated lactic acid bacteria of step (a):

In the step (b), the secondary coating is performed by mixing the functional hydrated hyaluronic acid and the primary coated lactic acid bacteria of the step (a). The functional hydrated hyaluronic acid is capable of controlling harmful bacteria in the intestines by combining fermented products of antibacterial lactic acid bacteria that inhibits harmful bacteria in the intestines.

The functional hydrated hyaluronic acid is mixed at a ratio of 0.001 to 1 part by weight relative to 100 parts by weight of the culture medium of lactic acid bacteria. Specifically, the mixing ratio of the functional hydrated hyaluronic acid is mixed with, for example, 0.001, 0.002, 0.003, 0.004, 0.005, 0.006, 0.007, 0.008, 0.009, 0.010, 0.011, 0.012, 0.013, 0.014, 0.015, 0.016, 0.017, 0.018, 0.019, 0.020, 0.021, 0.022, 0.023, 0.024, 0.025, 0.026, 0.027, 0.028, 0.029, 0.030, 0.031, 0.032, 0.033, 0.034, 0.035, 0.036, 0.037, 0.038, 0.039, 0.040, 0.041, 0.042, 0.043, 0.044, 0.045, 0.046, 0.047, 0.048, 0.049, 0.050, 0.051, 0.052, 0.053, 0.054, 0.055, 0.056, 0.057, 0.058, 0.059, 0.060, 0.061, 0.062, 0.063, 0.064, 0.065, 0.066, 0.067, 0.068, 0.069, 0.070, 0.071, 0.072, 0.073, 0.074, 0.075, 0.076, 0.077, 0.078, 0.079, 0.080, 0.081, 0.082, 0.083, 0.084, 0.085, 0.086, 0.087, 0.088, 0.089, 0.090, 0.091, 0.092, 0.093, 0.094, 0.095, 0.096, 0.097, 0.098, 0.099, 0.100 parts by weight of functional hydrated hyaluronic acid relative to 100 parts by weight of the culture medium of lactic acid bacteria. It is not limited to the above values as long as it is within the range of 0.001 to 1 part by weight relative to 100 parts by weight of the culture medium of lactic acid bacteria. Preferably, the functional hydrated hyaluronic acid is mixed at a ratio of 0.001 to 0.05 part by weight, and more preferably 0.001 to 0.005 part by weight relative to 100 parts by weight of the culture medium of lactic acid bacteria.

(c) conducting a tertiary coating by mixing a coating agent having porous particles with the secondarily coated lactic acid bacteria of step (b):

The porous coating agent is a coating agent of a base having porous particulate nature in the cells, and serves to block the inflow of external moisture and wet air. The porous particles can be used as the above-mentioned tertiary coating agent. They include, but are specially limited to, alginate, maltodextrin (MD), chitosan, starch, polyethyleneglycol (PEG), triacetin, propylene glycol, acetyl triethyl citrate, triethyl citrate and glycerin, preferably alginate, maltodextrin (MD) and polyethyleneglycol (PEG), and most preferably maltodextrin (MD).

The porous coating agent is mixed at a ratio of 0.1 to 10 parts by weight relative to 100 parts by weight of the culture medium of lactic acid bacteria. Specifically, the mixing ratio of the porous coated agent is, for example 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0 but is not limited to the above values if it is within the range of 0.1 to 10 parts by weight relative to 100 parts by weight of the culture medium of lactic acid bacteria.

Preferably, the porous coating agent is mixed at 0.1 to 5 parts by weight, and more preferably 0.1 to 0.5 parts by weight relative to 100 parts by weight of the culture medium of lactic acid bacteria.

Preferably, maltodextrin (MD) as the porous coating agent is mixed at a ratio of 0.1 to 10 parts by weight relative to 100 parts by weight of the culture medium of lactic acid bacteria. Specifically, the mixing ratio of MD is, for example, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, but is not limited to the above values if it is within the range of 0.1 to 10 parts by weight relative to 100 parts by weight of the culture medium of lactic acid bacteria.

Preferably, the MD is mixed with 0.1 to 5 parts by weight, and more preferably 0.1 to 0.5 part by weight relative to 100 parts by weight of the culture medium of lactic acid bacteria as the porous coating agent.

(d) conducting a quaternary coating by mixing a protein with the tertiary coated lactic acid bacteria of step (c):

The protein is mixed with the tertiary-coated lactic acid bacteria to fill the voids of the tertiary coating with a porous particle structure, but is not limited to, and is preferably a protein selected from the groups consisting of skimmed milk powder, whey protein, isolated soybean protein, and more preferably whey protein.

The protein as the quaternary coating agent is mixed at a ratio of 1 part by weight to 30 parts by weight of protein relative to 100 parts by weight of the culture medium of lactic acid bacteria. Specifically, the mixing ratio of protein as the quaternary coated agent is, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30. When the ratio is within the range of 1 to 30 parts by weight relative to 100 parts by weight of the culture medium of lactic acid bacteria, it is not limited to the above values. Preferably, the protein, which is the quaternary coating agent, is mixed at a ratio of 1 part by weight to 10 parts by weight, and most preferably 5 parts by weight to 10 parts by weight, based on 100 parts by weight of the culture medium of lactic acid bacteria.

Preferably, the a quaternary coating agent, the whey protein may be mixed at a ratio of 1 to 30 parts by weight of protein relative to 100 parts by weight of the culture medium of lactic acid bacteria. Specifically, for example, whey protein is mixed at a ratio of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, but it is not limited to the above values if the ratio is within the range of 1 to 30 parts by weight based on 100 parts by weight of the culture medium of lactic acid bacteria. Preferably, as the quaternary coating agent, the whey protein is mixed at a ratio of 1 to 10 parts by weight, and most preferably 5 to 10 parts by weight relative to 100 parts by weight of the culture medium of lactic acid bacteria.

The quadruply coated lactic acid bacteria produced by the method of the present invention have excellent adhesion to the intestinal mucosa as compared with conventional uncoated, single coated, dual coated, tertiary coated lactic acid bacteria as well as quadruple coated lactic acid bacteria. According to one example of the present invention, the quadruply coated lactic acid bacteria using the functional hydrated hyaluronic acid are superior to the conventional quadruple-coated lactic acid bacteria on adhesion to the intestinal mucosa in vitro and in vivo. This effect is very significant in that it is excellent even in the presence of resident flora in an environment similar to a human intestinal mucosa.

Meanwhile, in order for the coated lactic acid bacteria to adhere to the intestinal mucosa after reaching the host's intestine, they must compete with the host's resident flora. In addition, in order for lactic acid bacteria to adhere to the intestinal mucosa to exhibit beneficial physiological activity, it is preferable to suppress the growth of noxious bacteria in the intestinal mucosa and to promote the proliferation of beneficial bacteria. Therefore, it can be said that the quadruply coated lactic acid bacteria of the present invention is very superior to conventional uncoated, single coated, dual coated, tertiary coated and quadruple coated lactic acid bacteria. Specifically, according to one example of the present invention, since the quadruply coated lactic acid bacteria using the functional hydrated hyaluronic acid has a superior competitive inhibition ability to harmful bacteria compared to conventional uncoated or quadruply coated lactic acid bacteria, it was found that the ability of the lactic acid bacteria to enhance the intestinal mucosal adhesion can be improved even in the presence of resident flora. In addition, according to the method of the present invention, the functional hydrated hyaluronic acid, which is a secondary coating agent of quadruply coated lactic acid bacteria, has an effect of inhibiting proliferation of harmful bacteria while promoting the proliferation of beneficial bacteria. Thus it was found that the antagonistic effect was selectively exerted only on the harmful bacteria.

In addition to excellent adherence to the intestinal mucosa and selective antagonism against harmful bacteria, the quadruply coated lactic acid bacteria of the present invention are structurally stable due to the quadruple coating, effectively blocking external environmental factors such as moisture and air, and excellent in acid tolerance and bile tolerance.

The quadruply coated lactic acid bacteria of the present invention are also characterized in that it is prepared as described above. The quadruply coated lactic acid bacteria of the present invention maintain the excellent acid tolerance and bile tolerance of conventional quadruply coated lactic acid bacteria. In addition, compared with uncoated and quadruple coated lactic acid bacteria, it has excellent ability to inhibit harmful bacteria among intestinal flora, so that it can be efficiently normalized when harmful bacteria increase. It also contributes to the efficient normalization of intestinal microflora by helping the proliferation of lactic acid bacteria, which are beneficial bacteria in intestinal microflora.

According to another example of the present invention, when the functional hydrated hyaluronic acid of the present invention can be used as a coating agent for dual or tertiary coated lactic acid bacteria as well as a quadruply coated lactic acid bacterium, it showed much improved adhesion to the intestinal mucosa compared with that of lactic acid bacteria coated with conventional hyaluronic acid. Thus, it was found that functional hydration hyaluronic acid itself can be used as a coating agent exhibiting excellent adherence to the intestinal mucosa and antagonism against harmful bacteria.

In addition, dual or tertiary coated lactic acid bacteria using the functional hydrated hyaluronic acid of the present invention exhibited equivalent acid tolerance and bile acid tolerance as compared with dual or tertiary coated lactic acid bacteria using conventional hyaluronic acid, and it was suggested that the protective effect of lactic acid bacteria inherent in hyaluronic acid was maintained in the process of manufacturing the functional hydrated hyaluronic acid.

The lactic acid bacteria coated with the functional hydrated hyaluronic acid of the present invention not only exhibits the same degree of acid tolerance and bile tolerance as the lactic acid bacteria coated with conventional hyaluronic acid, but also exhibits excellent adhesion to the intestinal mucosa and selective antagonism against harmful bacteria. Such lactic acid bacterial coating agents and lactic acid bacteria coated methods have not been reported in the past, and the inventors of the present invention reported this effect by using the functional hydrated hyaluronic acid for coating of lactic acid bacteria, which is the first report in the present invention.

Effects of the Invention

The functional hydrated hyaluronic acid of the present invention has an effect of exhibiting a selective antagonism by exhibiting inhibiting proliferation of harmful bacteria and promoting proliferation of beneficial bacteria. The lactic acid bacteria coated with the functionalized hydrated hyaluronic acid of the present invention have an effect of exhibiting superior adhesion to the intestinal mucosa and selective antagonism against the harmful bacteria as compared with lactic acid bacteria coated with conventional hyaluronic acid.

Particularly, the functional hydrated hyaluronic acid of the present invention can be used as quadruply coated lactic acid bacteria by mixing lactic acid bacteria with a water soluble polymer, a functional hydrated hyaluronic acid, a coating agent having porous particles and a protein, and thus it not only exhibits excellent adhesion to the intestinal mucosa and selective antagonism against harmful bacteria which are not present in conventional uncoated, single, dual, tertiary and quadruple coated lactic acid bacteria, but also has excellent acid tolerance and bile tolerance. Therefore, it does not lose the physiological activity function inherent in lactic acid bacteria.

BRIEF DESCRIPTION OF THE DRAWINGS

FIG. 3 is a photograph showing evaluation of the proliferation promoting effect of *Lactobacillus rhamnosus*, which is a material of functional hydrated hyaluronic acid containing the culture medium of *Lactobacillus acidophilus* IDCC 3302 (A: control group of conventional hyaluronic acid treatment, B: treatment group of functional hydrated hyaluronic acid).

FIG. 4 is a photograph showing evaluation of the proliferation promoting effect of *Bifidobacterium longum*, which is a material of functional hydrated hyaluronic acid containing the culture medium of *Lactobacillus acidophilus* IDCC 3302 (A: control group of conventional hyaluronic acid treatment, B: treatment group of functional hydrated hyaluronic acid).

FIG. 5 is a photograph showing evaluation of the proliferation promoting effect of *Enterococcus faecium*, which is a material of functional hydrated hyaluronic acid containing the culture medium of *Lactobacillus acidophilus* IDCC 3302 (A: control group of conventional hyaluronic acid treatment, B: treatment group of functional hydrated hyaluronic acid).

MODE FOR CARRYING OUT INVENTION

Hereinafter, the present invention will be described an detail.

However, the following examples are illustrative of the present invention, and the present invention is not limited to the following examples.

Example 1

The Preparation of Functional Hydrated Hyaluronic Acid

The adhesion inhibitor against harmful bacteria, such as lipoteichoic acid and peptidoglycan which are representative components contained in the *Lactobacillus acidophilus* IDCC 3302 cell structure, and the lactic acid bacterial culture medium which inhibits the growth of harmful bacteria and promotes the growth of beneficial bacteria were complexed with hyaluronic acid. To do this, the *Lactobacillus acidophilus* IDCC 3302 broth was subjected to a pressure and heat treatment (pressure gauge of 1.2 atm) at 121° C. for 5 minutes, and the bacterial medium was cooled to 30° C. The bacterial medium was further a pressure and heat treatment at 110° C. for 10 minutes (pressure gauge of 0.8 atm), cooled to 30° C., and further a pressure and heat treatment at 80° C. for 30 minutes, and finally cooled to 30° C. to prepare an lactic acid bacteria medium that inhibits adhesion.

Figure 1:
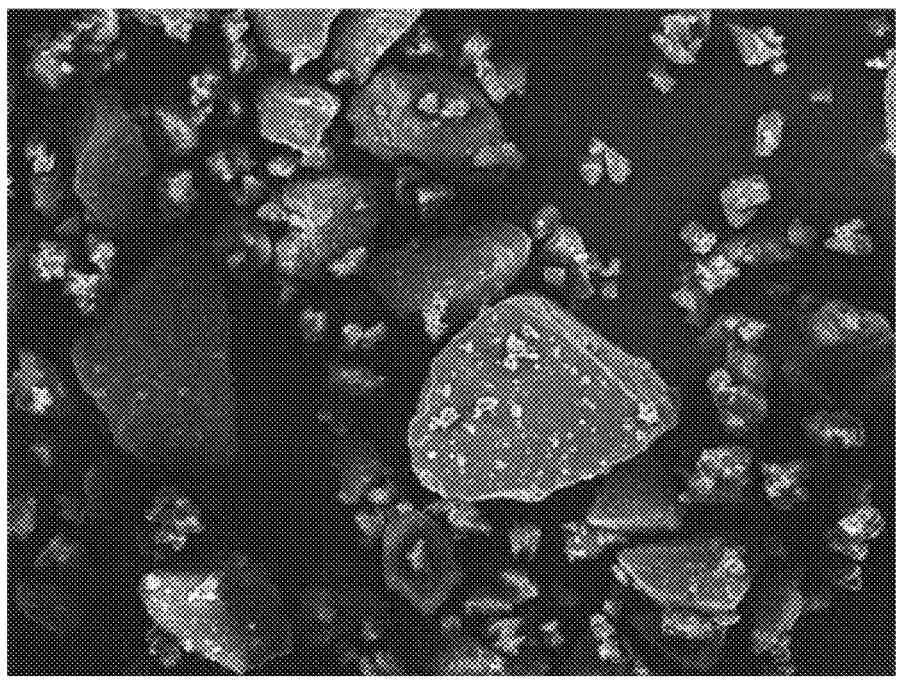
FIG. 1 is a photograph having the shape of functional hydrated hyaluronic acid.

The culture medium was concentrated by vacuum evaporation to $\frac{1}{10}$ of the initial volume at 60° C., and 0.01 to 1% (w/v) of hyaluronic acid was added thereto. After thoroughly stirring and dissolving, the culture was further concentrated by vacuum evaporation at 50° C. and dried. As shown in FIG. 1, a raw material of functional hydrated hyaluronic acid was prepared.

Example 2

Adhesion Inhibitory Ability of Functional Hydrated Hyaluronic Acid

In order to evaluate an ability of adhesion inhibitory of functional hydrated hyaluronic acid on harmful bacteria, an in vitro model of Caco-2 cell line, which is a human epithelial cell line, was used. The in vitro model of Caco-2 cell line shows mature intestinal cell characteristics such as polarization, functional brush border and hydrolytic enzyme secretion. Since it is necessary for the ligand of the lactic acid bacteria to interact with a specific receptor in order for the lactic acid bacteria to bind to the intestinal mucosa cells, Caco-2 cells in the intestines are known to be one of the most useful in vitro models for studying the intestinal fixation of lactic acid bacteria (Microbiol. 59(12):4121-4128, Gut. 35:483-489, and FEMS microbiology Lett. 91:213-218).

Specifically, when functionalized hyaluronic acid was first treated with Caco-2 cells and the *Salmonella typhimurium* KCTC 2054 as indicator bacteria was attached, the number of *Salmonella typhimurium* KCTC 2054 cells attached to Caco-2 cells was measured. This was converted to inhibition rate.

As a control group, conventional hyaluronic acid was used instead of the functional hydrated hyaluronic acid. More specifically, the Caco-2 cell monolayer was inoculated with $1.2 \times 10^5$ cells/ml of Caco-2 cells in DMEM added with 10% (v/v) fetal calf serum and 20 µl/ml gentamicin. The culture medium was aliquoted with 1 ml per well of tissue culture plate (BD, USA), cultured for 7 days, and then washed twice with phosphate buffered saline (PBS, pH 7.2). 0.5 ml of the functional hydrated hyaluronic acid solution was added to each well in which a Caco-2 monolayer was formed, and it was reacted for 90 minutes. A hyaluronic acid solution was used as a control. 0.5 ml ($1 \times 10^8$ cfu/ml) of *Salmonella typhimurium* KCTC 2054 sample was added thereto and reacted for 90 minutes. After the reaction, the supernatant was removed and Caco-2 cells were washed twice with PBS to remove unattached *Salmonella typhimurium* KCTC 2054. *Salmonella typhimurium* KCTC 2054 attached to Caco-2 cells was recovered by adding 1 ml of Tween 80 0.04% (w/v) and viable cells were counted. The results are shown in Table 1 below.

TABLE 1

| Adhesion inhibitory ability of *Salmonella typhimurium* KCTC 2054 on functional hydrated Hyaluronic acid | | |
|---|---|---|
| Classification | Control group - hyaluronic acid | Functional hydrated hyaluronic acid |
| Adhesion inhibition rate (%) of *Salmonella typhimurium* | <1% | 46% |

As shown in Table 1, the control hyaluronic acid showed almost no adhesion inhibition rate of *Salmonella typhimurium* while the functional hydrated hyaluronic acid showed 46% adhesion inhibition ratio. Thus, when the functional hydrated hyaluronic acid was used as a coating agent for lactic acid bacteria, lactic acid bacteria would be adhered to the intestinal mucosa and it would be helpful for competitive elimination with harmful bacteria in the intestines.

Example 3

Antagonism of Harmful Bacteria of Functional Hydrated Hyaluronic Acid

In order to evaluate the antibacterial activity against the harmful bacteria in the intestinal flora of functional hydration hyaluronic acid, the minimum inhibitory concentration (MIC) of *Salmonella typhimurium* KCTC 2054 was determined and the effects on the harmful bacteria in the intestinal flora were compared. The experimental method was modified by using the bacterial growth inhibition test suggested in the Korean Pharmacopoeia. The details are as follows.

1) Preparation of Test Solution of *Salmonella typhimurium* KCTC 2054

To prepare *Salmonella typhimurium* KCTC 2054 test solution, 1 loop of *Salmonella typhimurium* KCTC 2054 grown in Brain Heart Infusion agar (BHI agar, BD, USA) was suspended in 5 ml of sterilized BHI fluid medium to obtain 0.15 at $OD_{620\ nm}$. This solution was used as test solution.

2) Operation

Functional hydrated hyaluronic acid powder was added to 20 ml of BHI fluid medium to a concentration of 1 to 10% (w/v), and the suspension was stirred for 5 to 10 minutes.

The suspension was centrifuged (5,000 RPM/15 min) and the supernatant was filtered and sterilized with a membrane filter (0.45 um). 2 ml of the filtered and sterilized solution of each concentration was put into a sterilized 4 ml test tube and 2% (v/v) of *Salmonella typhimurium* KCTC 2054 test solution was inoculated. As a control, conventional hyaluronic acid was used instead of the functional hydrated hyaluronic acid. After inoculation, the cells were grown at 37° C. for 24 hours.

3) Judgment

The concentration at which the growth of the microorganism was observed was determined after the incubation for 24 hours, and the concentration value at that time was defined as the MIC value.

Figure 2:
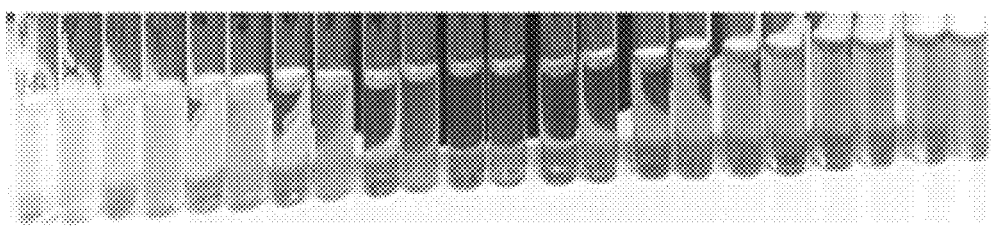
FIG. 2 shows the results of evaluation of the growth inhibitory ability of functional hydrated hyaluronic acid on *Salmonella typhimurium* KCTC 2054.

The results are shown in Table 2 and FIG. 2.

TABLE 2

Antagonism to *Salmonella typhimurium* KCTC 2054 of the functional hydrated hyaluronic acid

| Classification | Control group - hyaluronic acid | Functional hydrated hyaluronic acid |
|---|---|---|
| Concentration of minimum growth inhibition of *Salmonella typhimurium* | >10% | 4% (w/v) |

As shown in Table 2 and FIG. 2, the MIC value of the *Salmonella typhimurium* KCTC 2054 strain as a functional hydrated hyaluronic acid was evaluated. As a result, the functional hydrated hyaluronic acid showed a minimum inhibitory concentration (MIC) at a concentration of 4% (w/v), indicating the effect of inhibiting the growth of harmful bacteria.

Example 4

Proliferation Promoting Action of Beneficial Bacteria of Functional Hydration Hyaluronic Acid In order to evaluate the influence of beneficial bacteria of functional hydration hyaluronic acid, *Lactobacillus rhamnosus*, *Bifidobacterium longum*, *Enterococcus pneumatum*, and *Enterococcus faecium* represented by lactic acid bacteria were used. More specifically, for the preparation of the test bacterial culture medium of three kinds of intestinal beneficial bacteria, three kinds of beneficial bacteria grown in de Man-Rogosa-Sharpe agar (MRS, BD, USA) were suspended in the sterilized MRS culture medium and the suspension is used as a test.

The functional hydrated hyaluronic acid powder of *Lactobacillus acidophilus* IDCC 3302 is added to 20 ml of the MRS fluid medium to a concentration of 4% (w/v), and the suspension is stirred for 5 to 10 minutes. As a control group, normal hyaluronic acid was used instead of functional hydrated hyaluronic acid powder.

After centrifugation of the suspension (5,000 RPM/15 min), supernatant is filtered and sterilized with membrane filter (0.45 um). 2 ml of filtered and sterilized solution was put into a sterile 4 ml test tube and three kinds of beneficial bacteria were inoculated in 2% (v/v) each. After the inoculation, while the cultures were incubated at 37° C. for 24 hours, the growth of the bacteria was observed under a microscope to compare the degree of proliferation with the control group. The results are shown in FIGS. 3 to 5.

As shown in FIGS. 3 to 5, in the *Lactobacillus rhamnosus* (FIG. 3), *Bifidobacterium longum* (FIG. 4) and *Enterococcus faecium* (FIG. 5) treated with functional hydrated hyaluronic acid according to the present invention, it was confirmed that the growth of each bacteria was promoted as compared with the control group treated with conventional hyaluronic acid.

Example 5

Selection of Crosslinking Agents for Surface Coated of Lactic Acid Bacteria

The most suitable coated crosslinking agent was selected by evaluating the crosslinking ability of the water-soluble polymer forming the surface of the lactic acid bacteria and the functional hydrated hyaluronic acid. More specifically, a solution of functional hydrated hyaluronic acid dissolved in a concentration of 4 g/l and a solution of a water-soluble polymer dissolved in a concentration of 1% (w/v) in a third distilled water were mixed at a volume ratio of 1:1 (v/v). The mixture was stirred vigorously for 1 minute, and then left at room temperature for 30 minutes. The crosslinking affinity was determined by comparing with the result obtained by mixing only the third distilled water with the functional hydrated hyaluronic acid. When crosslinking is formed, the average molecular weight of the functional hydrated hyaluronic acid increases and the viscosity of the solution increases. The viscosity was measured and compared by measuring the time required for descent through a certain section using ViscoClock (SI Analytics) by adding the solution to a viscometer (Ubbelogdevisceter, SI analytics) whose measurement time increased with increasing viscosity in a constant temperature water bath at 24° C. (Table 3).

As can be seen in Table 3 below, the functional hydrated hyaluronic acid formed a good crosslinking with all the water-soluble polymers used in the experiment, and was found to form the best crosslinking with carboxymethylcellulose (CMC) in particular.

TABLE 3

Selection of crosslinking agents for surface coated of lactic acid bacteria

| Classification | Control group | Chitosan | Polyvinyl Pyrrolidone | CMC | Gum Arabic |
|---|---|---|---|---|---|
| Descendant time (sec) | 548 | 584 | 595 | 625 | 560 |

To determine the optimum concentration of CMC which is a coated crosslinking agent that best forms the crosslinking with functional hydration hyaluronic acid, the functional hydrated hyaluronic acid was dissolved in tertiary distilled water at a concentration of 4 g/L to prepare a solution by adding CMC from 0.1 to 0.4% (w/v). ViscoClock was used to comparatively compare the crosslinking formation, and the time required to descend through a certain section was measured to compare the relative viscosity The results are shown in Table 4 below.

TABLE 4

Optimal CMC concentration for crosslinking with functional hydrated hyaluronic acid

| | Concentration (w/v) | | | | |
|---|---|---|---|---|---|
| | None | 0.1% | 0.2% | 0.3% | 0.4% |
| Descendant time (sec) | 548 | 625 | 632 | 583 | 567 |

As shown in Table 4, the optimal CMC concentration for the crosslinking with functional hydration hyaluronic acid showed a descending time of 632 sec when 0.2% (w/v) was used, indicating that the crosslinking ability was excellent.

Example 6

Dual Coated Lactic Acid Bacteria Using the Functional Hydrated Hyaluronic Acid

<6-1> Preparation of Functional Hydrated Dual Coated Lactic Acid Bacteria

In the present invention, on the basis of the preparation method of the coated lactic acid bacteria described in an example of the Korean patent (No. 10-1280232), functional hydrated dual coated lactic acid bacteria were sequentially prepared by using CMC-Na, a surface thin film coating agent of the lactic acid bacteria as a primary coating agent and using hyaluronic acid as a secondary coating agent prepared in the example 1. As a control group, dual coated lactic acid bacteria were prepared using conventional hyaluronic acid instead of functional hydrated hyaluronic acid.

<6-2> Acid Tolerance of Functional Hydrate Dual Coated Lactic Acid Bacteria

After lactic acid bacteria are orally ingested, they are exposed to gastric juice when they pass through the stomach of the digestive organs of the human body. This similar environment is prepared under the conditions of a test tube, and the survival rate of dual coated lactic acid bacteria using the functional hydrated hyaluronic acid and dual coated lactic acid bacteria using conventional hyaluronic acid was compared to evaluate the acid tolerance.

More specifically, 10% HCl was added to the MRS medium to titrate the pH to 2.3 and 2.5, followed by sterilization. 1 g of the sample was added to the MRS medium adjusted to the each pH value, and reacted for 0 hours, 1 hour and 2 hours. After that, viable cells were counted. The lactic acid bacteria used in the experiment were 12 *Lactobacillus* sp., four *Bifidobacterium* sp., one *Streptococcus* sp., one *Enterococcus* sp, one *Lactococcus* sp. They were manufactured as dual coated lactic acid bacteria using the functional hydrated hyaluronic acid and dual coated lactic acid bacteria using hyaluronic acid, respectively, and then the manufactured dual coated lactic acid bacteria were compared each other.

The results are shown in Table 5 below.

TABLE 5

Acid tolerance results of functional hydrated hyaluronic acid dual coated lactic acid bacteria

| Coating | Microorganism | pH 2.3 ($\times 10^8$ CFU/g) | | | | pH 2.5 ($\times 10^8$ CFU/g) | | | |
|---|---|---|---|---|---|---|---|---|---|
| | | 0 Hr | 1 Hr | 2 Hr | Viability (%) | 0 시간 | 1 시간 | 2 시간 | Viability (%) |
| Dual coating using hyaluronic acid | *Lactobacillus acidophilus* IDCC 3302 | 130 | 91 | 71 | 55 | 130 | 101 | 74 | 57 |
| | *Lactobacillus bulgaricus* | 125 | 82 | 62 | 50 | 125 | 92 | 67 | 54 |
| | *Lactobacillus casei* | 145 | 95 | 75 | 52 | 145 | 105 | 81 | 56 |
| | *Lactobacillus fermentum* | 122 | 82 | 64 | 53 | 122 | 92 | 68 | 56 |
| | *Lactobacillus gasseri* | 148 | 89 | 74 | 50 | 148 | 99 | 79 | 54 |
| | *Lactobacillus helveticus* | 160 | 92 | 83 | 52 | 160 | 98 | 88 | 55 |
| | *Lactobacillus johnsonii* | 120 | 71 | 57 | 48 | 120 | 81 | 60 | 50 |
| | *Lactobacillus paracasei* | 130 | 89 | 71 | 55 | 130 | 99 | 74 | 57 |
| | *Lactobacillus plantarum* | 122 | 83 | 69 | 57 | 122 | 93 | 73 | 60 |
| | *Lactobacillus reuteri* | 132 | 77 | 58 | 44 | 132 | 87 | 64 | 49 |
| | *Lactobacillus rhamnosus* | 144 | 91 | 79 | 55 | 144 | 101 | 80 | 56 |
| | *Lactobacillus salivarius* | 121 | 81 | 62 | 52 | 121 | 91 | 64 | 53 |
| | *Bifidobacterium bifidum* | 132 | 82 | 67 | 51 | 132 | 92 | 73 | 56 |
| | *Bifidobacterium breve* | 142 | 87 | 76 | 54 | 142 | 97 | 82 | 58 |
| | *Bifidobacterium lactis* | 124 | 75 | 64 | 52 | 124 | 85 | 73 | 59 |
| | *Bifidobacterium longum* | 142 | 93 | 82 | 58 | 142 | 102 | 88 | 62 |
| | *Enterococcus faecium* | 152 | 90 | 79 | 52 | 152 | 101 | 86 | 57 |
| | *Lactococcus lactis* | 105 | 81 | 52 | 50 | 105 | 91 | 61 | 59 |
| | *Streptococcus thermophilus* | 102 | 55 | 44 | 44 | 102 | 65 | 52 | 51 |
| Dual coating using functional | *Lactobacillus acidophilus* IDCC 3302 | 120 | 71 | 60 | 50 | 120 | 81 | 64 | 54 |
| | *Lactobacillus* | 115 | 62 | 51 | 45 | 115 | 72 | 58 | 51 |

TABLE 5-continued

Acid tolerance results of functional hydrated hyaluronic acid dual coated lactic acid bacteria

| Coating | Microorganism | pH 2.3 (×10⁸ CFU/g) | | | | pH 2.5 (×10⁸ CFU/g) | | | |
|---|---|---|---|---|---|---|---|---|---|
| | | 0 Hr | 1 Hr | 2 Hr | Viability (%) | 0 시간 | 1 시간 | 2 시간 | Viability (%) |
| hydrated hyaluronic acid | bulgaricus | | | | | | | | |
| | Lactobacillus casei | 125 | 72 | 60 | 48 | 125 | 82 | 65 | 52 |
| | Lactobacillus fermentum | 112 | 69 | 52 | 47 | 112 | 79 | 59 | 53 |
| | Lactobacillus gasseri | 138 | 71 | 60 | 44 | 138 | 81 | 69 | 50 |
| | Lactobacillus helveticus | 120 | 62 | 55 | 46 | 120 | 72 | 61 | 51 |
| | Lactobacillus johnsonii | 110 | 55 | 46 | 42 | 110 | 65 | 57 | 52 |
| | Lactobacillus paracasei | 110 | 58 | 47 | 43 | 110 | 68 | 59 | 54 |
| | Lactobacillus plantarum | 112 | 62 | 56 | 50 | 112 | 72 | 59 | 53 |
| | Lactobacillus reuteri | 122 | 57 | 48 | 40 | 122 | 67 | 57 | 47 |
| | Lactobacillus rhamnosus | 124 | 70 | 60 | 49 | 124 | 80 | 52 | 42 |
| | Lactobacillus salivarius | 102 | 52 | 42 | 42 | 102 | 62 | 48 | 48 |
| | Bifidobacterium bifidum | 112 | 58 | 48 | 43 | 112 | 68 | 60 | 54 |
| | Bifidobacterium breve | 122 | 62 | 53 | 44 | 122 | 72 | 67 | 55 |
| | Bifidobacterium lactis | 104 | 56 | 47 | 46 | 104 | 76 | 58 | 56 |
| | Bifidobacterium longum | 122 | 67 | 58 | 48 | 122 | 77 | 73 | 60 |
| | Enterococcus faecium | 123 | 60 | 51 | 42 | 123 | 70 | 68 | 56 |
| | Lactococcus lactis | 101 | 58 | 47 | 47 | 101 | 68 | 54 | 54 |
| | Streptococcus thermophilus | 103 | 43 | 39 | 38 | 103 | 63 | 47 | 46 |

As shown in Table 5, the acid tolerance of dual coated lactic acid bacteria using the functional hydrated hyaluronic acid and dual coated lactic acid bacteria using the conventional hyaluronic acid were compared to each other. As a result, it showed similar acid tolerance in each experimental group.

These results suggest that the characteristic of hyaluronic acid which protects lactic acid bacteria was not destroyed during the preparation of functional hydrated hyaluronic acid.

<6-3> Bile Tolerance of Dual Coated Lactic Acid Bacteria Using the Functional Hydrated Hyaluronic Acid Bile acid is made in the liver, flows out into the small intestine of the bile ducts, and is absorbed again by the ileum at the end of the small intestine. This process affects lactic acid bacteria that have settled in the small intestine.

Thus, the survival rates of dual coated lactic acid bacteria using the functional hydrated hyaluronic acid and dual coated lactic acid bacteria using hyaluronic acid were compared in vitro when exposed to bile acids. More specifically, 0.3% of bile acid was added to the culture medium or not and the both culture media were sterilized. Each medium was inoculated with 1 g each of dual coated lactic acid bacteria using the functional hydrated hyaluronic acid and dual coated lactic acid bacteria using hyaluronic acid as a control group. After incubation for 5 hours, viable cells were counted to compare the bile tolerance.

The results are shown in Table 6 below.

TABLE 6

Bile tolerance results of dual coated lactic acid bacteria using the functional hydrated hyaluronic acid

| Coating | Microorganism | MRS | MRS + 0.3% bile | Viablity(%) |
|---|---|---|---|---|
| Dual coating using hyaluronic acid | Lactobacillus acidophilus IDCC 3302 | 230 | 147 | 64 |
| | Lactobacillus bulgaricus | 160 | 105 | 66 |
| | Lactobacillus casei | 150 | 97 | 65 |
| | Lactobacillus fermentum | 170 | 115 | 68 |
| | Lactobacillus gasseri | 172 | 115 | 67 |
| | Lactobacillus helveticus | 168 | 109 | 65 |
| | Lactobacillus johnsonii | 194 | 126 | 65 |
| | Lactobacillus paracasei | 215 | 129 | 60 |
| | Lactobacillus plantarum | 227 | 131 | 58 |
| | Lactobacillus reuteri | 168 | 104 | 62 |

TABLE 6-continued

Bile tolerance results of dual coated lactic acid bacteria using the functional hydrated hyaluronic acid

| Coating | Microorganism | MRS | MRS + 0.3% bile | Viablity(%) |
|---|---|---|---|---|
| | Lactobacillus rhamnosus | 175 | 119 | 68 |
| | Lactobacillus salivarius | 168 | 109 | 65 |
| | Bifidobacterium bifidum | 215 | 137 | 64 |
| | Bifidobacterium breve | 200 | 110 | 55 |
| | Bifidobacterium lactis | 225 | 121 | 54 |
| | Bifidobacterium longum | 220 | 125 | 57 |
| | Enterococcus faecium | 135 | 74 | 55 |
| | Lactococcus lactis | 121 | 72 | 60 |
| | Streptococcus thermophilus | 110 | 63 | 58 |
| Dual coating using functional hydrated hyaluronic acid | Lactobacillus acidophilus IDCC 3302 | 220 | 149 | 68 |
| | Lactobacillus bulgaricus | 150 | 100 | 67 |
| | Lactobacillus casei | 140 | 91 | 65 |
| | Lactobacillus fermentum | 166 | 112 | 68 |
| | Lactobacillus gasseri | 152 | 97 | 64 |
| | Lactobacillus helveticus | 148 | 97 | 66 |
| | Lactobacillus johnsonii | 124 | 80 | 65 |
| | Lactobacillus paracasei | 115 | 69 | 60 |
| | Lactobacillus plantarum | 127 | 74 | 58 |
| | Lactobacillus reuteri | 158 | 97 | 62 |
| | Lactobacillus rhamnosus | 165 | 112 | 68 |
| | Lactobacillus salivarius | 148 | 96 | 65 |
| | Bifidobacterium bifidum | 115 | 73 | 64 |
| | Bifidobacterium breve | 100 | 55 | 55 |
| | Bifidobacterium lactis | 125 | 67 | 54 |
| | Bifidobacterium longum | 120 | 76 | 64 |
| | Enterococcus faecium | 145 | 95 | 66 |
| | Lactococcus lactis | 131 | 85 | 65 |
| | Streptococcus thermophilus | 120 | 127 | 58 |

As shown in Table 6 above, the bile tolerance of dual coated lactic acid bacteria using the functional hydrated hyaluronic acid and dual coated lactic acid bacteria using the conventional hyaluronic acid was compared each other, and the bile tolerance in each experimental group was similar with almost no difference. Therefore, the functional hydrate hyaluronic acid was not destroyed during the manufacturing process, and thus it is considered that similar effect of functional hydrated hyaluronic acid was observed after coating with lactic acid bacteria.

<6-4> Non-Competitive Adhesion of Functional Hydrated Dual Coated Lactic Acid Bacteria The Caco-2 cell monolayer was inoculated with $1.2 \times 10^5$ cells/ml of Caco-2 cells in Dulbecco's Modified Eagle's Medium (DMEM, Hyclone, USA) added with 10% (v/v) fetal calf serum and 20 μl/ml gentamicin. The solution was aliquoted with 1 ml per well of tissue culture plate (BD, USA), cultured for 7 days, and then washed twice with phosphate buffered saline (PBS, pH 7.2).

1 ml of uncoated lactic acid bacteria, hyaluronic acid dual coated lactic acid bacteria, and functional hydrated hyaluronic acid dual coated lactic acid bacteria were placed in each well where Caco-2 monolayer was formed and they were reacted for 90 minutes. The dual coated lactic acid bacteria were prepared based on the dual coated lactic acid bacteria preparation method of Korean Patent No. 10-1280232.

After the reaction, the supernatant was removed and 1 ml of Tween 80 0.04% (w/v) was added to recover the sample of lactic acid bacteria attached to Caco-2 cells, and the number of bacteria to be observed using a hemocytometer was measured. Adhesion efficiency was calculated by the ratio of the number of adhering bacteria to the initial number of bacteria.

The results are shown in Table 7 below.

As shown in Table 7 below, the adhesion efficiency of hyaluronic acid dual coated lactic acid bacteria was relatively higher than that of uncoated lactic acid bacteria in the evaluation of adhesion to Caco-2 cells similar to the intestinal membrane, and the adhesion efficiency of dual coated lactic acid bacteria using the functional hydrated hyaluronic acid was higher than that of dual coated lactic acid bacteria using the hyaluronic acid.

TABLE 7

Non-competing ability of dual coated lactic acid bacteria using the functional hydrate hyaluronic acid

| | Attachment of Lactic Acid Bacteria (%) | | |
|---|---|---|---|
| Classification | Un-coated | Hyaluronic acid Dual coated | Functional hydrated hyaluronic acid dual coated |
| Lactobacillus acidophilus IDCC 3302 | 26 | 44 | 48 |
| Lactobacillus bulgaricus | 5 | 27 | 29 |
| Lactobacillus casei | 8 | 31 | 34 |
| Lactobacillus fermentum | 5 | 24 | 28 |
| Lactobacillus gasseri | 12 | 26 | 28 |
| Lactobacillus helveticus | 15 | 28 | 34 |
| Lactobacillus johnsonii | 35 | 47 | 54 |
| Lactobacillus paracasei | 17 | 33 | 40 |
| Lactobacillus plantarum | 15 | 29 | 35 |
| Lactobacillus reuteri | 8 | 15 | 18 |
| Lactobacillus rhamnosus | 34 | 52 | 56 |
| Lactobacillus salivarius | 5 | 14 | 20 |
| Bifidobacterium bifidum | 13 | 28 | 33 |
| Bifidobacterium breve | 17 | 34 | 42 |
| Bifidobacterium lactis | 24 | 35 | 40 |
| Bifidobacterium longum | 23 | 33 | 38 |
| Enterococcus faecium | 38 | 54 | 55 |
| Lactococcus lactis | 32 | 45 | 48 |
| Streptococcus thermophilus | 14 | 26 | 32 |

When there were no microorganisms competing with lactic acid bacteria in the intestinal mucosa cells, the basic intestinal mucosal adhesiveness showed overall improved adhesion efficiency in dual coated lactic acid bacteria using the functionalized hydrated hyaluronic acid as compared with dual coated lactic acid bacteria using the conventional hyaluronic acid. From these results, it was found that the intestinal mucosal adhesion effect of functional hydrated hyaluronic acid was equivalent or improved to that of conventional hyaluronic acid, so that the inherent intestinal mucosal adhesion of hyaluronic acid was not destroyed during the preparation of the functional hydrated hyaluronic acid.

<6-5> Competitive Exclusion of the Functional Hydrated Dual Coated Lactic Acid Bacteria In general, in order for lactic acid bacteria to enhance an intestinal regulation in the intestines, the ability of the lactic acid bacteria to bind to intestinal mucosa should be better than that of *Escherichia coli* and *Salmonella* to bind to the intestinal mucosa. However, lactic acid bacteria, which are classified as Gram-positive bacteria are less able to bind to intestinal mucosa than Gram-negative bacteria such as *Escherichia coil* and *Salmonella*. Therefore, in order to more clearly determine whether dual coated lactic acid bacteria using the functional hydrated hyaluronic acid can exhibit beneficial physiological activity in the intestines, the present inventors sought to evaluate the adherence ability of the lactic acid bacteria in the presence of resident flora.

To perform the comparative test of the adhesion ability in the presence of resident flora, the number of *Salmonella typhimurium* KCTC 2054 cells attached to Caco-2 cells was measured. After *Salmonella typhimurium* KCTC 2054 as indicator bacteria was first attached to Caco-2 cells, the uncoated, lactic acid bacterium coated by hyaluronic acid, and dual coated lactic acid bacteria using the functional hydrated hyaluronic acid were treated. This measurement was converted to the inhibition rate.

More specifically, the Caco-2 cell monolayer was inoculated with $1.2 \times 10^5$ cells/ml of Caco-2 cells in Dulbecco's Modified Eagle's Medium (DMEM, Hyclo ne, USA) added with 10% (v/v) fetal calf serum and 20 µl/ml gentamicin. The culture medium was aliquoted with 1 ml per well of tissue culture plate (BD, USA), cultured for 7 days, and then washed twice with phosphate buffered saline (PBS, pH 7.2).

*Salmonella typhimurium* KCTC 2054 were collected by centrifuging 10 ml of brain heart infusion (BHI, BD, USA), washed twice with phosphate buffer saline, resuspended with 1 ml of phosphate buffer saline, and diluted by serum-free DMEM at a concentration of $1 \times 10^8$ CFU/ml. *Salmonella typhimurium* KCTC 2054 (0.5 ml) was placed in each well in which Caco-2 monolayer was formed, and allowed to react for 60 minutes. After the reaction, lactic acid bacteria ($1 \times 10^8$ CFU/ml) were treated in the same amount and reacted for 90 minutes.

To measure the viable count of *Salmonella typhimurium* KCTC 2054 attached to Caco-2 cells, 1 ml of Tween 80 0.04% (w/v) was added to recover *Salmonella typhimurium* KCTC 2054 from the Caco-2 cells, and the number of viable cells was measured in BG agar medium.

The adhesion inhibition ratio of *Salmonella typhimurium* KCTC 2054 was calculated as follows.

[Adhesion inhibition ratio of *Salmonella typhimurium* adhesion (%)]

[1−(Number of adhesive of *Salmonella typhimurium* in the test group/Number of adhesive of *Salmonella typhimurium* in DMEM×100(%)

The results are shown in Table 8 below.

As shown in Table 8 below, *Salmonella typhimurium* KCTC 2054, which is a harmful microorganism, was first attached to Caco-2 cells similar to intestinal membranes. The harmful bacteria are competitive with the uncoated, hyaluronic acid dual coating, and dual coated lactic acid bacteria using the functional hydrated hyaluronic acid. As a result of comparing the removal rates of the harmful bacteria, uncoated lactic acid bacteria that do not contain functional substances have relatively low removal efficiency because they remove *Salmonella typhimurium* KCTC 2054 by a competition removal method. The dual coated lactic acid bacteria using the functional hydrated hyaluronic acid showed significantly higher removal efficiency of the harmful bacteria than the uncoated and hyaluronic acid dual coated lactic acid bacteria.

Meanwhile, dual coated lactic acid bacteria using the functional hydrated hyaluronic acid showed direct antibacterial activity against the attached *Salmonella typhimurium* KCTC 2054 in addition to competitive elimination. Therefore, *Salmonella typhimurium* was smoothly removed from. Caco-2 cells, and dual coated lactic acid bacteria using the functional hydrated hyaluronic acid were shown to be well-settled at the site where harmful bacteria were desorbed by hyaluronic acid.

Meanwhile, the effect of dual coated lactic acid bacteria using the functionalized hydrated hyaluronic acid was 47% superior to that of the uncoated lactic acid bacteria in the result of *Lactobacillus acidophilus* IDCC 3302, and it also showed an excellent effect of 33% or more even in comparison with the conventional hyaluronic acid dual coated lactic acid bacteria. Thus, when functional hydrated hyaluronic acid is used as a coating agent of lactic acid bacteria, it has been found that the inhibitory effect against harmful bacteria in the intestines is remarkably improved as compared with conventional coating agents of lactic acid bacteria.

TABLE 8

Competitive exclusion of the functional hydrated dual coated lactic acid bacteria

| | Competitive exclusion of *Salmonella typhimurium* (%) | | |
|---|---|---|---|
| Classification | Un-coated | Hyaluronic acid Dual coated | Functional hydrated hyaluronic acid dual coated |
| *Lactobacillus acidophilus* IDCC 3302 | 31 | 45 | 78 |
| *Lactobacillus bulgaricus* | 22 | 37 | 67 |
| *Lactobacillus casei* | 38 | 52 | 82 |
| *Lactobacillus fermentum* | 26 | 39 | 58 |
| *Lactobacillus gasseri* | 32 | 36 | 62 |
| *Lactobacillus helveticus* | 20 | 34 | 54 |
| *Lactobacillus johnsonii* | 27 | 58 | 82 |
| *Lactobacillus paracasei* | 21 | 45 | 62 |
| *Lactobacillus plantarum* | 24 | 32 | 47 |
| *Lactobacillus reuteri* | 23 | 42 | 58 |
| *Lactobacillus rhamnosus* | 33 | 48 | 68 |
| *Lactobacillus salivarius* | 11 | 23 | 52 |
| *Bifidobacterium bifidum* | 16 | 25 | 42 |
| *Bifidobacterium breve* | 15 | 24 | 35 |
| *Bifidobacterium lactis* | 18 | 22 | 38 |
| *Bifidobacterium longum* | 22 | 27 | 41 |
| *Enterococcus faecium* | 35 | 42 | 74 |
| *Lactococcus lactis* | 24 | 36 | 69 |
| *Streptococcus thermophilus* | 13 | 27 | 47 |

<6-6> In Vivo Intestinal Fixation of Dual Coated Lactic Acid Bacteria Using the Functional Hydrated Hyaluronic Acid For the in vivo intestinal fixation of dual coated lactic acid bacteria using functional hydrated hyaluronic acid, five 4-weeks old ICR mice were used for each test. In particular, this experiment was carried out for selecting an experimental group effective for restoration of *Lactobacilli* among intestinal flora after disturbing intestinal flora by administration of antibiotics.

The experimental groups consisted of uncoated lactic acid bacteria, dual coated lactic acid bacteria using hyaluronic acid, dual coated lactic acid bacteria using the functional hydrated hyaluronic acid, and control group without lactic acid bacteria. The experimental period was 6 weeks and the first 0.5 week was the adaptation period of the experimental animals. 0.4 g/l ampicillin per day was given in drinking water for one week after the adaptation period.

For the next 2 weeks, lactic acid bacteria were orally administered, and the number of bacteria was $1\times10^{10}$ CFU/g. As a control group, PBS was orally administered instead of lactic acid bacteria. During the next 2.5 weeks, the administration of lactic acid bacteria was discontinued and intestinal flora changes were observed. Fecal samples were collected twice a week during the entire test period. The number of *Lactobacilli* in experiment groups was counted on LBS (*Lactobacillus* selective media, BD, USA) agar medium.

Figure 6:
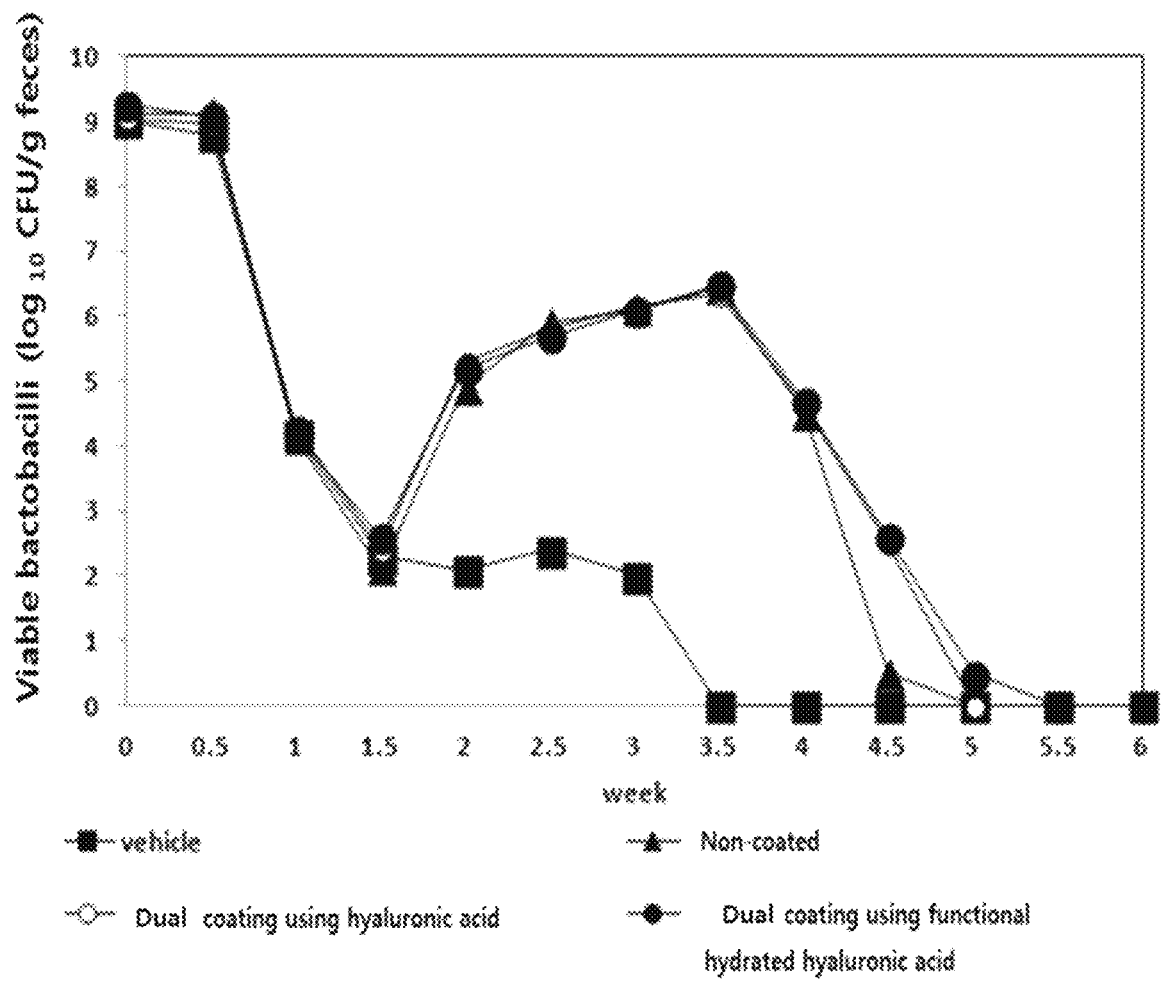
FIG. 6 compares intestinal fixation of dual coated *Lactobacillus acidophilus* IDCC 3302 using functional hydration hyaluronic acid, and dual coated *Lactobacillus acidophilus* IDCC 3302 using conventional hyaluronic acid and uncoated *Lactobacillus acidophilus* IDCC 3302.

The results are shown in FIG. 6.

As shown in FIG. 6, it was confirmed that *lacto-bacillus* bacteria were detected in the feces up to 2.5 weeks after discontinuation of the treatment with dual coated lactic acid bacteria using the hyaluronic acid and dual coated lactic acid bacteria using the functional hydrated hyaluronic acid compared with the uncoated lactic acid bacteria. However, because of the structure of the coated lactic acid bacteria based on hyaluronic acid alone, it is vulnerable to gastric acid and bile acid. Therefore, both groups showed similar intestinal fixation pattern.

<6-7> In Vivo Harmful Bacteria Inhibition of Dual Coated Lactic Acid Bacteria Using Functional Hydrated Hyaluronic Acid Antibacterial activity was investigated in a mouse model infected with *Salmonella typhimurium* KCTC 2054 in order to confirm the ability of dual coated lactic acid bacteria using the functional hydrated hyaluronic acid to inhibit harmful bacteria in vivo.

Six weeks old female ICR mice (6 mice/cage) were divided into four groups: uncoated lactic acid bacteria, dual coated lactic acid bacteria using the hyaluronic acid, dual coated lactic acid bacteria using the functional hydrated hyaluronic acid, and PBS (vehicle) treatment. The mice were given 0.2% (w/v) tetracycline at a dose of 200 μl/mouse/day for one week to suppress and disturbed intestinal flora. After 1 week, *Salmonella typhimurium* KCTC 2054 ($1\times10^8$ CFU/ml) was orally administered at the rate of 200 μl/mouse/day for the first 3 days of the sample administration period and four samples were also orally administered at 200 μl/mouse/day for 2 weeks at a concentration of $1\times10^{10}$ CFU/g. For the next 2.5 weeks, the sample administration was discontinued and the growth inhibition changes of the pest were observed. Fecal samples were collected from each experimental group twice a week during the entire test period and *Salmonella* bacteria were analyzed on BG agar medium.

Figure 7:
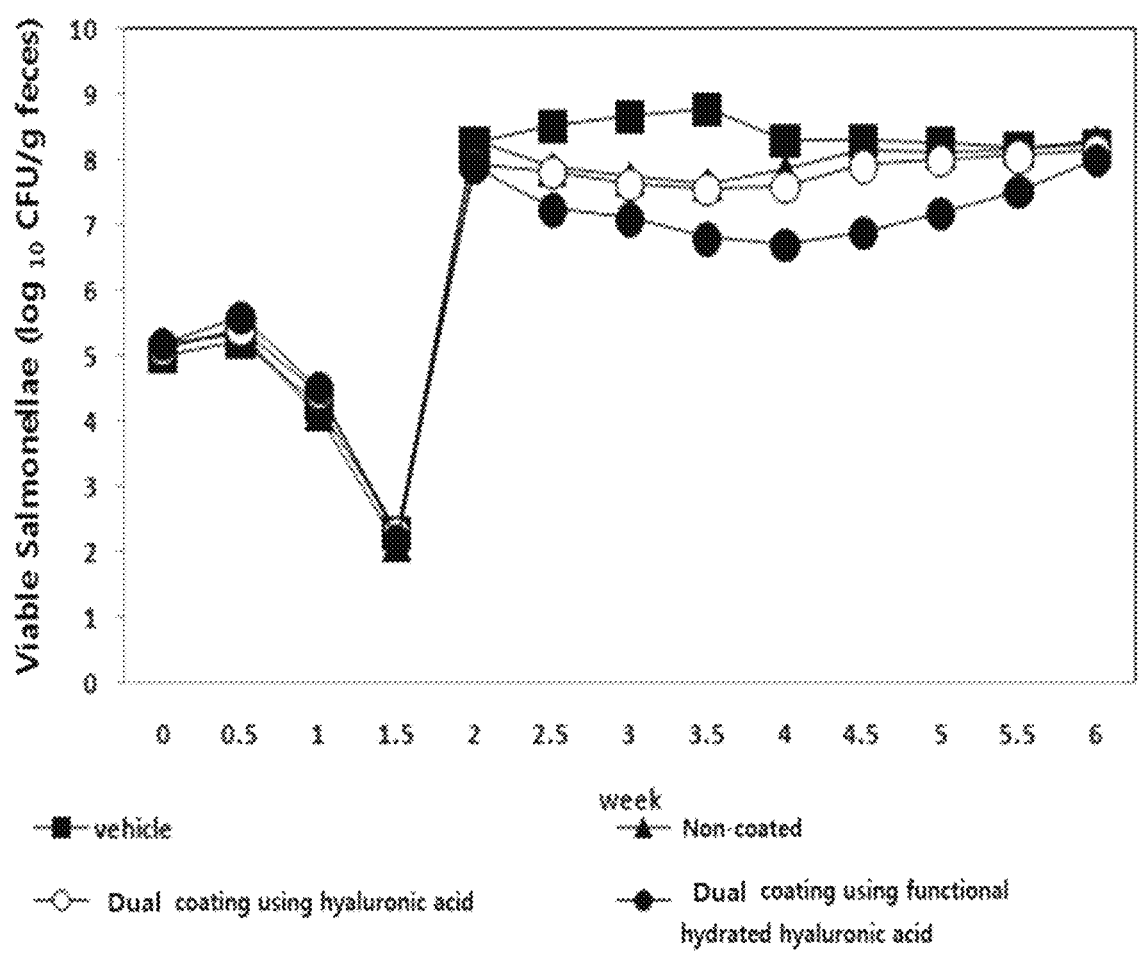
FIG. 7 is a diagram evaluating the effect of dual coated *Lactobacillus acidophilus* IDCC 3302 using functional hydration hyaluronic acid, and dual coated *Lactobacillus acidophilus* IDCC 3302 using conventional hyaluronic acid and uncoated *Lactobacillus acidophilus* IDCC 3302 on the growth of intestinal *Salmonella*.

The results are shown in FIG. 7.

As shown in FIG. 7, as a result of administration of uncoated, dual coated lactic acid bacteria using hyaluronic acid, and dual coated lactic acid bacteria using the functional hydrated hyaluronic acid to a mouse model which inhibited resident flora by antibiotics and was infected with *Salmonella typhimurium* KCTC 2054, it was found that the growth of the uncoated and dual coated lactic acid bacteria using hyaluronic acid, which plays a role of exclusion of simple competition, was inhibited by competing with *Salmonella typhimurium* KCTC 2054, but dual coated lactic acid bacteria using the functional hydrated hyaluronic acid inhibited. *Salmonella typhimurium* KCTC 2054 more than 10 times more efficiently by antagonism and competitive exclusion.

Example 7

Tertiary Coated Lactic Acid Bacteria Using the Functional Hydrated Hyaluronic Acid <7-1> Preparation of Functional Hydrated Tertiary Coated Lactic Acid Bacteria In the present invention, on the basis of the preparation method of the coated lactic acid bacteria described in an example of the Korean patent (No. 10-1280232), the functional hydrated tertiary coated lactic acid bacteria were sequentially prepared by using CMC-Na which is a surface thin film coating agent of the lactic acid bacteria as a primary coating agent, using hyaluronic acid as a secondary coating agent prepared in the example 1, and using maltodextrin as a tertiary coating agent. As a control group, the hyaluronic acid tertiary coated lactic acid bacteria were prepared using conventional hyaluronic acid instead of the functional hydrated hyaluronic acid.

<7-2> Acid Tolerance of Tertiary Coated Lactic Acid Bacteria Using Functional Hydrated Hyaluronic Acid Acid tolerance is exposed to gastric juice when they pass through the stomach of the digestive organs of the human body. This similar environment is prepared under the conditions of a test tube, and the survival rate of tertiary coated lactic acid bacteria using the functional hydrated hyaluronic acid and tertiary coated lactic acid bacteria using hyaluronic acid was compared to evaluate the acid tolerance [Table 9]. The experiment was carried out in the same manner as in Example <6-2> of the present invention.

The results are shown in Table 9 below.

TABLE 9

Acid tolerance results of the functional hydrated tertiary coated lactic acid bacteria

| | | pH 2.3 ($\times 10^8$ CFU/g) | | | | pH 2.5 ($\times 10^8$ CFU/g) | | | |
| --- | --- | --- | --- | --- | --- | --- | --- | --- | --- |
| Coating | Microorganism | 0 Hr | 1 Hr | 2 Hr | Viablity (%) | 0 Hr | 1 Hr | 2 Hr | Viability (%) |
| Tertiary coating using hyaluronic acid | *Lactobacillus acidophilus* IDCC 3302 | 140 | 111 | 84 | 60 | 140 | 121 | 90 | 64 |
| | *Lactobacillus bulgaricus* | 135 | 102 | 75 | 56 | 135 | 112 | 81 | 60 |
| | *Lactobacillus casei* | 155 | 115 | 91 | 59 | 155 | 127 | 96 | 62 |
| | *Lactobacillus fermentum* | 132 | 102 | 79 | 60 | 132 | 112 | 83 | 63 |

TABLE 9-continued

Acid tolerance results of the functional hydrated tertiary coated lactic acid bacteria

| Coating | Microorganism | pH 2.3 (×10⁸ CFU/g) | | | | pH 2.5 (×10⁸ CFU/g) | | | |
|---|---|---|---|---|---|---|---|---|---|
| | | 0 Hr | 1 Hr | 2 Hr | Viablity (%) | 0 Hr | 1 Hr | 2 Hr | Viability (%) |
| | *Lactobacillus gasseri* | 158 | 109 | 91 | 58 | 158 | 129 | 103 | 65 |
| | *Lactobacillus helveticus* | 170 | 112 | 102 | 60 | 170 | 118 | 105 | 62 |
| | *Lactobacillus johnsonii* | 140 | 93 | 88 | 63 | 140 | 101 | 94 | 67 |
| | *Lactobacillus paracasei* | 150 | 110 | 85 | 57 | 150 | 119 | 98 | 65 |
| | *Lactobacillus plantarum* | 132 | 105 | 68 | 52 | 132 | 113 | 79 | 60 |
| | *Lactobacillus reuteri* | 142 | 97 | 69 | 49 | 142 | 107 | 84 | 59 |
| | *Lactobacillus rhamnosus* | 154 | 113 | 90 | 59 | 154 | 121 | 95 | 62 |
| | *Lactobacillus salivarius* | 141 | 103 | 78 | 56 | 141 | 111 | 85 | 60 |
| | *Bifidobacterium bifidum* | 142 | 105 | 79 | 56 | 142 | 112 | 88 | 62 |
| | *Bifidobacterium breve* | 162 | 105 | 93 | 58 | 162 | 117 | 102 | 63 |
| | *Bifidobacterium lactis* | 144 | 97 | 82 | 57 | 144 | 105 | 94 | 65 |
| | *Bifidobacterium longum* | 162 | 115 | 102 | 63 | 162 | 122 | 104 | 64 |
| | *Enterococcus faecium* | 162 | 110 | 93 | 58 | 162 | 121 | 100 | 62 |
| | *Lactococcus lactis* | 135 | 104 | 72 | 54 | 135 | 111 | 78 | 58 |
| | *Streptococcus thermophilus* | 122 | 77 | 61 | 50 | 122 | 85 | 63 | 52 |
| Tertiary coating using functional hydrated hyaluronic acid | *Lactobacillus acidophilus* IDCC 3302 | 136 | 91 | 78 | 58 | 136 | 101 | 84 | 62 |
| | *Lactobacillus bulgaricus* | 131 | 82 | 70 | 54 | 131 | 92 | 76 | 58 |
| | *Lactobacillus casei* | 151 | 94 | 84 | 56 | 151 | 102 | 86 | 57 |
| | *Lactobacillus fermentum* | 127 | 90 | 74 | 59 | 127 | 99 | 79 | 62 |
| | *Lactobacillus gasseri* | 154 | 93 | 84 | 55 | 154 | 101 | 97 | 63 |
| | *Lactobacillus helveticus* | 165 | 84 | 97 | 59 | 165 | 90 | 102 | 62 |
| | *Lactobacillus johnsonii* | 134 | 77 | 81 | 61 | 134 | 85 | 87 | 65 |
| | *Lactobacillus paracasei* | 145 | 78 | 81 | 56 | 145 | 88 | 91 | 63 |
| | *Lactobacillus plantarum* | 127 | 86 | 64 | 51 | 127 | 92 | 75 | 59 |
| | *Lactobacillus reuteri* | 136 | 79 | 61 | 45 | 136 | 87 | 72 | 53 |
| | *Lactobacillus rhamnosus* | 150 | 90 | 84 | 56 | 150 | 100 | 93 | 62 |
| | *Lactobacillus salivarius* | 138 | 75 | 74 | 54 | 138 | 82 | 83 | 60 |
| | *Bifidobacterium bifidum* | 139 | 78 | 73 | 53 | 139 | 88 | 86 | 62 |
| | *Bifidobacterium breve* | 152 | 72 | 79 | 52 | 152 | 102 | 88 | 58 |
| | *Bifidobacterium lactis* | 138 | 79 | 70 | 51 | 138 | 96 | 81 | 59 |
| | *Bifidobacterium longum* | 152 | 89 | 91 | 60 | 152 | 97 | 103 | 68 |
| | *Enterococcus faecium* | 150 | 82 | 78 | 52 | 150 | 90 | 93 | 62 |
| | *Lactococcus lactis* | 125 | 78 | 62 | 51 | 136 | 88 | 105 | 56 |
| | *Streptococcus thermophilus* | 112 | 67 | 53 | 48 | 127 | 83 | 95 | 54 |

As shown in Table 9, the acid tolerance of tertiary coated lactic acid bacteria using the functional hydrated hyaluronic acid and tertiary coated lactic acid bacteria using conventional hyaluronic acid were compared to each other, and the results were equivalent to those of tertiary coated lactic acid bacteria using conventional hyaluronic acid. These results suggest that the characteristic of hyaluronic acid which protects lactic acid bacteria was not destroyed during the production of functional hydrated hyaluronic acid.

Meanwhile, when the results of the above table are compared only with the results of *Lactobacillus acidophilus* IDCC 3302, tertiary coated lactic acid bacteria using conventional hyaluronic acid showed acid tolerance of 60% (pH 2.3) and 64% (pH 2.5). This was higher than the acid tolerance of 50% of dual coated lactic acid bacteria using the hyaluronic acid in the above example <6-2>, and it was found that the coated effect was correlated with the acid tolerance. Thus, the tertiary coating showed better acid tolerance than the dual coating, and the protective effect of the coated was reflected in the acidic survival rate.

<7-3> Bile Tolerance Results of the Functional Hydrated Tertiary Coated Lactic Acid Bacteria The survival rates of tertiary coated lactic acid bacteria using the functional hydrated hyaluronic acid and tertiary coated lactic acid bacteria using hyaluronic acid were compared in vitro when exposed to bile acids. The experiment was carried out in the same manner as in Example <6-3> of the present invention.

The results are shown in Table 10 below.

TABLE 10

Bile tolerance results of tertiary coated lactic acid bacteria using the functional hydrated hyaluronic acid

| Coating | Microorganism | MRS | MRS + 0.3% bile | Viability(%) |
|---|---|---|---|---|
| Tertiary coating using hyaluronic acid | Lactobacillus acidophilus IDCC 3302 | 245 | 181 | 74 |
| | Lactobacillus bulgaricus | 160 | 121 | 76 |
| | Lactobacillus casei | 180 | 135 | 75 |
| | Lactobacillus fermentum | 182 | 141 | 78 |
| | Lactobacillus gasseri | 168 | 130 | 77 |
| | Lactobacillus helveticus | 152 | 114 | 75 |
| | Lactobacillus johnsonii | 144 | 99 | 69 |
| | Lactobacillus paracasei | 152 | 103 | 68 |
| | Lactobacillus plantarum | 172 | 116 | 68 |
| | Lactobacillus reuteri | 210 | 144 | 69 |
| | Lactobacillus rhamnosus | 258 | 185 | 72 |
| | Lactobacillus salivarius | 190 | 161 | 75 |
| | Bifidobacterium bifidum | 243 | 170 | 70 |
| | Bifidobacterium breve | 255 | 163 | 64 |
| | Bifidobacterium lactis | 229 | 148 | 65 |
| | Bifidobacterium longum | 240 | 158 | 66 |
| | Enterococcus faecium | 260 | 187 | 72 |
| | Lactococcus lactis | 185 | 114 | 62 |
| | Streptococcus thermophilus | 151 | 96 | 64 |
| Tertiary coating using functional hydrated hyaluronic acid | Lactobacillus acidophilus IDCC 3302 | 235 | 164 | 70 |
| | Lactobacillus bulgaricus | 150 | 105 | 70 |
| | Lactobacillus casei | 170 | 122 | 72 |
| | Lactobacillus fermentum | 162 | 116 | 72 |
| | Lactobacillus gasseri | 178 | 135 | 72 |
| | Lactobacillus helveticus | 142 | 106 | 70 |
| | Lactobacillus johnsonii | 134 | 84 | 63 |
| | Lactobacillus paracasei | 142 | 88 | 62 |
| | Lactobacillus plantarum | 162 | 98 | 61 |
| | Lactobacillus reuteri | 193 | 121 | 63 |
| | Lactobacillus rhamnosus | 232 | 157 | 68 |
| | Lactobacillus salivarius | 172 | 111 | 65 |
| | Bifidobacterium bifidum | 224 | 134 | 60 |
| | Bifidobacterium breve | 215 | 133 | 62 |
| | Bifidobacterium lactis | 219 | 137 | 62 |
| | Bifidobacterium longum | 210 | 130 | 62 |
| | Enterococcus faecium | 220 | 143 | 65 |
| | Lactococcus lactis | 175 | 107 | 58 |
| | Streptococcus thermophilus | 131 | 78 | 60 |

As shown in Table 10, when the bile tolerance of the tertiary coated lactic acid bacteria using the functional hydrated hyaluronic acid was compared with that of tertiary coated lactic acid bacteria using hyaluronic acid during exposing of bile acid for 5 hours, they showed similar survival rates of about 70%. These results suggest that the characteristic of hyaluronic acid which protects lactic acid bacteria was not destroyed during the production of the functional hydrated hyaluronic acid.

<7-4> Non-Competitive Adhesion of Tertiary Coated Lactic Acid Bacteria Using Functional Hydrated Hyaluronic Acid The tertiary coated lactic acid bacteria were prepared on the basis of the tertiary coated lactic acid bacteria preparation method of Korean Patent No. 10-1280232 in order to compare the non-competitive adhesion ability in the absence of competitive microorganisms. In addition, in order to evaluate the non-competitive adhesion, the same procedure as in Example <6-4> of the present invention was performed.

The results are shown in Table 11 below.

As shown in the following Table 11, the adhesion efficiency of tertiary coated lactic acid bacteria using the functional hydrated hyaluronic acid and tertiary coated lactic acid bacteria using the hyaluronic acid was relatively better than that of uncoated lactic acid bacteria in Caco-2 cells similar to the intestinal membrane. The adhesion efficiency of tertiary coated lactic acid bacteria using the functional hydrated hyaluronic acid was higher than that of tertiary coated lactic acid bacteria using the hyaluronic acid.

TABLE 11

Non-competitive adhesion of tertiary coated lactic acid bacteria using the functional hydrated hyaluronic acid

| | Adhesion of lactic acid bacteria (%) | | |
|---|---|---|---|
| Classification | Un-coated | Hyaluronic acid tertiary coating | Functional hydrated hyaluronic acid tertiary coating |
| Lactobacillus acidophilus IDCC 3302 | 26 | 54 | 56 |
| Lactobacillus bulgaricus | 5 | 37 | 42 |
| Lactobacillus casei | 8 | 41 | 47 |
| Lactobacillus fermentum | 5 | 34 | 39 |
| Lactobacillus gasseri | 12 | 36 | 40 |
| Lactobacillus helveticus | 15 | 38 | 43 |
| Lactobacillus johnsonii | 35 | 57 | 63 |
| Lactobacillus paracasei | 17 | 43 | 55 |
| Lactobacillus plantarum | 15 | 39 | 43 |
| Lactobacillus reuteri | 8 | 25 | 36 |
| Lactobacillus rhamnosus | 34 | 62 | 64 |
| Lactobacillus salivarius | 5 | 24 | 35 |
| Bifidobacterium bifidum | 13 | 38 | 46 |
| Bifidobacterium breve | 17 | 44 | 53 |
| Bifidobacterium lactis | 24 | 45 | 57 |
| Bifidobacterium longum | 23 | 43 | 49 |
| Enterococcus faecium | 38 | 59 | 62 |
| Lactococcus lactis | 32 | 55 | 64 |
| Streptococcus thermophilus | 14 | 36 | 48 |

<7-5> Competitive Exclusion of the Functional Hydrated Tertiary Coated Lactic Acid Bacteria In order to more clearly determine whether tertiary coated lactic acid bacteria using the functional hydrated hyaluronic acid can exhibit beneficial physiological activity in the intestines, the present inventors were carried out in the same manner as in Example <6-5> of the present invention to evaluate the adherence ability of the lactic acid bacteria in the presence of resident flora.

The results are shown in Table 12 below.

As shown in Table 12 below, Salmonella typhimurium KCTC 2054, which is a harmful microorganism, was first attached to Caco-2 cells similar to intestinal membranes. The harmful bacteria are competitive with the uncoated, hyaluronic acid tertiary coating, and tertiary coated lactic acid bacteria using the functional hydrated hyaluronic acid. As a result of comparing the removal rates of the harmful bacteria, uncoated lactic acid bacteria that do not contain functional substances have relatively low removal efficiency because they remove Salmonella typhimurium KCTC 2054 by a competition removal method. The tertiary coated lactic acid bacteria using the functional hydrated hyaluronic acid showed significantly higher removal efficiency of the harmful bacteria than the uncoated and hyaluronic acid tertiary coated lactic acid bacteria.

Meanwhile, the effect of the tertiary coated lactic acid bacteria using the functional hydrated hyaluronic acid was 51% superior to that of the uncoated lactic acid bacteria in the result of Lactobacillus acidophilus IDCC 3302, and it also showed an excellent effect of 27% or more even in comparison with the conventional hyaluronic acid tertiary coated lactic acid bacteria. Thus, if the functional hydrated hyaluronic acid is used as a coating agent for lactic acid bacteria, it has been found that the inhibitory effect against harmful bacteria in the intestines is remarkably improved as compared with conventional lactic acid bacteria coating agents.

TABLE 12

Competitive exclusion of tertiary coated lactic acid bacteria using the functional hydrated hyaluronic acid

| | Competitive exclusion of Salmonella typhimurium (%) | | |
|---|---|---|---|
| Classification | Un-coated | Hyaluronic acid tertiary coating | Functional hydrated hyaluronic acid tertiary coating |
| Lactobacillus acidophilus IDCC 3302 | 31 | 55 | 82 |
| Lactobacillus bulgaricus | 22 | 47 | 72 |
| Lactobacillus casei | 38 | 62 | 88 |
| Lactobacillus fermentum | 26 | 49 | 68 |
| Lactobacillus gasseri | 32 | 46 | 72 |
| Lactobacillus helveticus | 20 | 54 | 64 |
| Lactobacillus johnsonii | 27 | 68 | 85 |
| Lactobacillus paracasei | 21 | 55 | 72 |
| Lactobacillus plantarum | 24 | 42 | 57 |
| Lactobacillus reuteri | 23 | 52 | 68 |
| Lactobacillus rhamnosus | 33 | 58 | 78 |
| Lactobacillus salivarius | 11 | 43 | 62 |
| Bifidobacterium bifidum | 16 | 45 | 52 |
| Bifidobacterium breve | 15 | 44 | 55 |
| Bifidobacterium lactis | 18 | 42 | 68 |
| Bifidobacterium longum | 22 | 47 | 59 |
| Enterococcus faecium | 35 | 54 | 64 |
| Lactococcus lactis | 24 | 56 | 63 |
| Streptococcus thermophilus | 13 | 47 | 56 |

<7-6> In Vivo Intestinal Fixation of Tertiary Coated Lactic Acid Bacteria Using the Functional Hydrated Hyaluronic Acid For the in vivo intestinal fixation test of tertiary coated lactic acid bacteria using the functional hydrated hyaluronic acid, the same experiment as in Example <6-6> of the present invention was performed.

Figure 8:
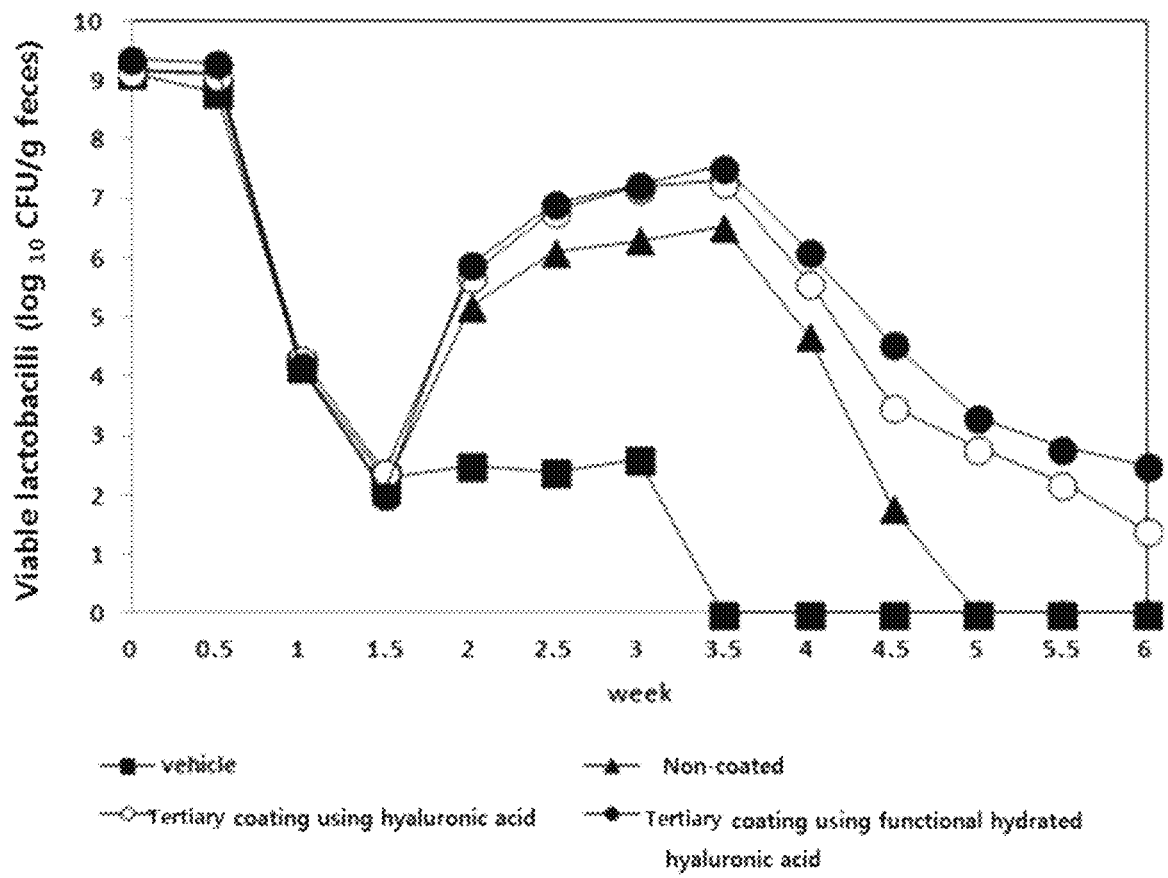
FIG. 8 is a diagram comparing intestinal fixation of tertiary coated *Lactobacillus acidophilus* IDCC 3302 using functional hydration hyaluronic acid, and tertiary coated *Lactobacillus acidophilus* IDCC 3302 using conventional hyaluronic acid and uncoated *Lactobacillus acidophilus* IDCC 3302.

The results are shown in FIG. 8.

As shown in FIG. 8, it was confirmed that Lactobacillus bacteria were detected in the feces up to 2.5 weeks after discontinuation of the treatment with tertiary coated lactic acid bacteria using hyaluronic acid and tertiary coated lactic acid bacteria using the functional hydrated hyaluronic acid compared with the uncoated lactic acid bacteria. The effect was confirmed to be the best in the tertiary coated lactic acid bacteria using the functional hydrated hyaluronic acid.

On the other hand, Lactobacillus was detected in the feces for up to one week after discontinuation of the uncoated lactic acid bacteria, and it was confirmed that the best fixing performance was obtained since the tertiary coated lactic acid bacteria using the functional hydrated hyaluronic acid group was detected by extending 1.5 weeks further.

Particularly, the tertiary coated lactic acid bacteria using the functional hydrated hyaluronic acid were not only the adherence of the intestinal mucosa through competitive exclusion but also proliferated, and Lactobacillus sp. was detected at a level of $1 \times 10^3$ CFU. Thus, the tertiary coated lactic acid bacteria using the functional hydrated hyaluronic acid may play a role in proliferating beneficial bacteria among intestinal microflora disturbed by antibiotic and Salmonella typhimurium.

<7-7> In Vivo Harmful Bacteria Inhibition with Tertiary Coated Lactic Acid Bacteria Using the Functional Hydrated Hyaluronic Acid In order to confirm the inhibitory ability of harmful bacteria with tertiary coated lactic acid bacteria using the functional hydrated hyaluronic acid in vivo, the antimicrobial activity in the mouse model infected with *Salmonella typhimurium* KCTC 2054 was performed in the same manner as in Example <6-7> of the present invention.

Figure 9:
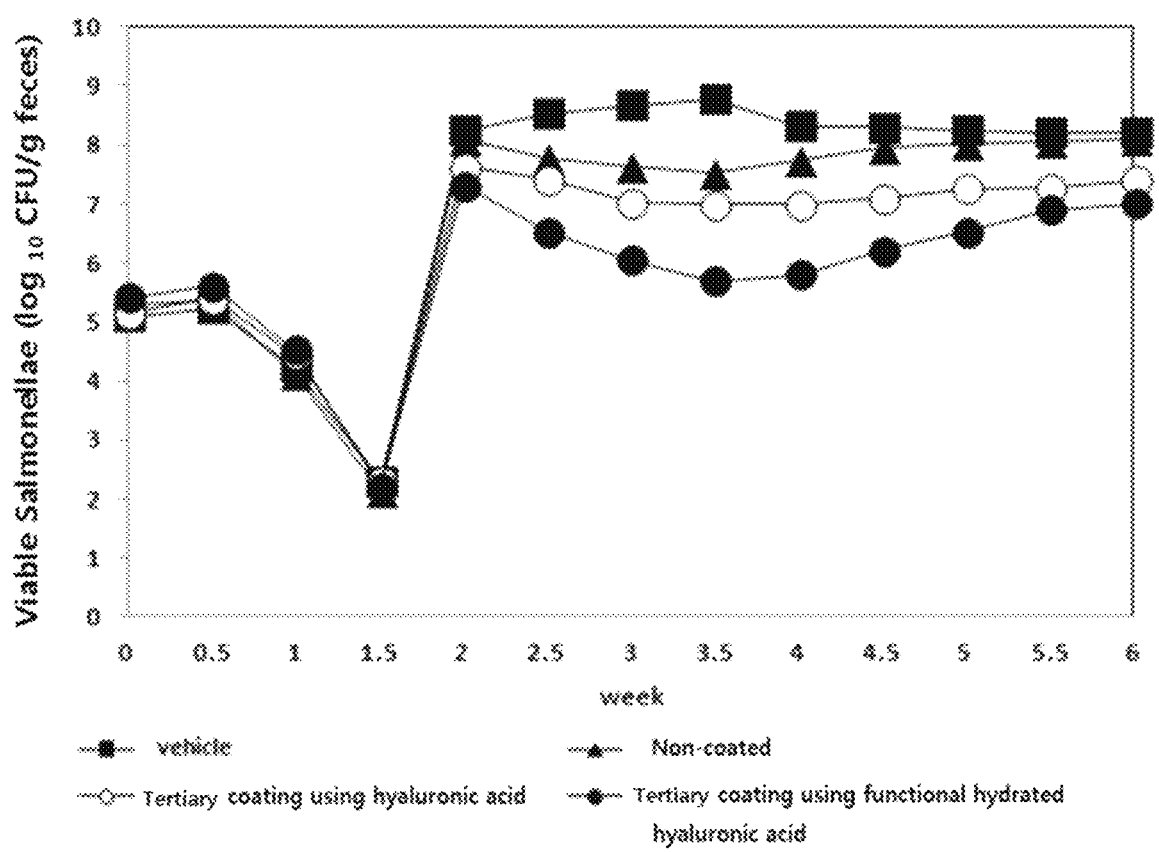
FIG. 9 is a diagram evaluating the effect of tertiary coated *Lactobacillus acidophilus* IDCC 3302 using functional hydration hyaluronic acid, and tertiary coated *Lactobacillus acidophilus* IDCC 3302 using conventional hyaluronic acid and uncoated *Lactobacillus acidophilus* IDCC 3302 on the growth of intestinal *Salmonella*.

The results are shown in FIG. 9.

As shown in FIG. 9, as a result of administration of uncoated, tertiary coated lactic acid bacteria using the hyaluronic acid, and tertiary coated lactic acid bacteria using the functional hydrated hyaluronic acid to a mouse model which inhibited resident flora by antibiotics and was infected with *Salmonella typhimurium* KCTC 2054, it was found that the growth of the uncoated and tertiary coated lactic acid bacteria using hyaluronic acid, which plays a role of exclusion of simple competition, was inhibited by competing with *Salmonella typhimurium* KCTC 2054, but tertiary coated lactic acid bacteria using the functional hydrated hyaluronic acid inhibited *Salmonella typhimurium* KCTC 2054 more efficiently for a long time.

This result shows that because the antifungal activity and competition exclusion of the intestinal microflora of the mice disturbed by the antibiotic and *Salmonella typhimurium* KCTC 2054 as competing bacteria are performed by tertiary coated lactic acid bacteria using the functional hydrated hyaluronic acid, it was confirmed that the growth of harmful bacteria is reduced by the antibacterial activity and competition exclusion. Thus the intestinal environment was rapidly normalized by increasing the proliferation of the beneficial bacteria.

Example 8

Quadruply Coated Lactic Acid Bacteria Using the Functional Hydrated Hyaluronic Acid <8> Preparation of Quadruply Coated Lactic Acid Bacteria Using the Functional Hydrated Hyaluronic Acid In the present invention, on the basis of the preparation method of the quadruply coated lactic acid bacteria described in an example of the Korean patent (No. 10-1280232), quadruply coated lactic acid bacteria using the functional hydrated hyaluronic acid were sequentially prepared by using CMC-Na which is a surface thin film coated agent of the lactic acid bacteria as a primary coating agent, using hyaluronic acid as a secondary coating agent prepared in the example 1, using maltodextrin as a tertiary coated agent and using whey protein as a final quaternary coating agent. As a control group, hyaluronic acid quadruple coated lactic acid bacteria were prepared using conventional hyaluronic acid instead of the functional hydrated hyaluronic acid.

<8-2> Acid Tolerance of Quadruple Coated Lactic Acid Bacteria Using the Functional Hydrated Hyaluronic Acid Acid tolerance is exposed to gastric juice when they pass through the stomach of the digestive organs of the human body. This similar environment is prepared under the conditions of a test tube, and the survival rate of quadruply coated lactic acid bacteria using the functional hydrated hyaluronic acid and quadruply coated lactic acid bacteria using the hyaluronic acid was compared to evaluate the acid tolerance. The experiment was carried out in the same manner as in Example <6-2> of the present invention.

The results are shown in Table 13 below.

TABLE 13

Acid tolerance results of quadruply coated lactic acid bacteria using the functional hydrated hyaluronic acid

| Coating | Microorganism | pH 2.3 ($\times 10^8$ CFU/g) | | | | pH 2.5 ($\times 10^8$ CFU/g) | | | |
|---|---|---|---|---|---|---|---|---|---|
| | | 0 Hr | 1 Hr | 2 Hr | Viability (%) | 0 Hr | 1 Hr | 2 Hr | Viability (%) |
| Quadruple coating using hyaluronic acid | *Lactobacillus acidophilus* IDCC 3302 | 150 | 121 | 105 | 70 | 150 | 131 | 123 | 82 |
| | *Lactobacillus bulgaricus* | 145 | 112 | 96 | 66 | 145 | 132 | 125 | 86 |
| | *Lactobacillus casei* | 175 | 125 | 121 | 69 | 175 | 155 | 140 | 80 |
| | *Lactobacillus fermentum* | 142 | 112 | 114 | 80 | 142 | 132 | 116 | 82 |
| | *Lactobacillus gasseri* | 178 | 129 | 121 | 68 | 178 | 149 | 132 | 74 |
| | *Lactobacillus helveticus* | 190 | 122 | 137 | 72 | 190 | 162 | 150 | 79 |
| | *Lactobacillus johnsonii* | 160 | 103 | 118 | 74 | 160 | 143 | 134 | 84 |
| | *Lactobacillus paracasei* | 170 | 120 | 117 | 69 | 170 | 140 | 134 | 79 |
| | *Lactobacillus plantarum* | 162 | 115 | 110 | 68 | 162 | 135 | 126 | 78 |
| | *Lactobacillus reuteri* | 152 | 107 | 94 | 62 | 152 | 137 | 125 | 82 |
| | *Lactobacillus rhamnosus* | 164 | 123 | 118 | 72 | 164 | 143 | 134 | 82 |
| | *Lactobacillus salivarius* | 161 | 113 | 119 | 74 | 161 | 143 | 135 | 84 |
| | *Bifidobacterium bifidum* | 152 | 115 | 109 | 72 | 152 | 135 | 125 | 82 |
| | *Bifidobacterium breve* | 172 | 115 | 134 | 78 | 172 | 155 | 151 | 88 |

TABLE 13-continued

Acid tolerance results of quadruply coated lactic acid bacteria using the functional hydrated hyaluronic acid

| Coating | Microorganism | pH 2.3 (×10⁸ CFU/g) | | | | pH 2.5 (×10⁸ CFU/g) | | | |
|---|---|---|---|---|---|---|---|---|---|
| | | 0 Hr | 1 Hr | 2 Hr | Viability (%) | 0 Hr | 1 Hr | 2 Hr | Viability (%) |
| | *Bifidobacterium lactis* | 164 | 107 | 118 | 72 | 164 | 147 | 134 | 82 |
| | *Bifidobacterium longum* | 182 | 125 | 133 | 73 | 182 | 165 | 151 | 83 |
| | *Enterococcus faecium* | 172 | 120 | 127 | 74 | 172 | 150 | 144 | 84 |
| | *Lactococcus lactis* | 155 | 114 | 105 | 68 | 155 | 144 | 136 | 88 |
| | *Streptococcus thermophilus* | 142 | 97 | 88 | 62 | 142 | 117 | 102 | 72 |
| Quadruple coating using functional hydrated hyaluronic acid | *Lactobacillus acidophilus* IDCC 3302 | 146 | 111 | 100 | 69 | 146 | 121 | 112 | 77 |
| | *Lactobacillus bulgaricus* | 141 | 92 | 85 | 60 | 141 | 122 | 97 | 69 |
| | *Lactobacillus casei* | 172 | 134 | 112 | 65 | 172 | 144 | 129 | 75 |
| | *Lactobacillus fermentum* | 138 | 100 | 95 | 69 | 138 | 120 | 109 | 79 |
| | *Lactobacillus gasseri* | 172 | 123 | 112 | 65 | 172 | 133 | 129 | 75 |
| | *Lactobacillus helveticus* | 181 | 144 | 127 | 70 | 181 | 154 | 136 | 75 |
| | *Lactobacillus johnsonii* | 172 | 147 | 120 | 70 | 172 | 157 | 131 | 76 |
| | *Lactobacillus paracasei* | 169 | 128 | 110 | 65 | 169 | 138 | 127 | 75 |
| | *Lactobacillus plantarum* | 160 | 126 | 104 | 65 | 160 | 136 | 120 | 75 |
| | *Lactobacillus reuteri* | 144 | 99 | 86 | 60 | 144 | 109 | 99 | 69 |
| | *Lactobacillus rhamnosus* | 152 | 110 | 103 | 68 | 152 | 120 | 114 | 75 |
| | *Lactobacillus salivarius* | 158 | 125 | 111 | 70 | 158 | 135 | 117 | 74 |
| | *Bifidobacterium bifidum* | 142 | 118 | 92 | 65 | 142 | 128 | 97 | 68 |
| | *Bifidobacterium breve* | 162 | 132 | 123 | 76 | 162 | 142 | 133 | 82 |
| | *Bifidobacterium lactis* | 155 | 129 | 109 | 70 | 155 | 139 | 118 | 76 |
| | *Bifidobacterium longum* | 172 | 139 | 124 | 72 | 172 | 149 | 132 | 77 |
| | *Enterococcus faecium* | 161 | 122 | 116 | 72 | 161 | 132 | 126 | 78 |
| | *Lactococcus lactis* | 142 | 108 | 92 | 65 | 142 | 128 | 105 | 74 |
| | *Streptococcus thermophilus* | 139 | 97 | 83 | 60 | 139 | 117 | 95 | 68 |

As shown in Table 13, the acid tolerance of the quadruply coated lactic acid bacteria using the functional hydrated hyaluronic acid showed higher acid tolerance than that of the conventional dual and tertiary coated lactic acid bacteria, and showed higher acid tolerance at pH 2.5. These results are believed to be due to the high acid tolerance effect inherent in quadruply coated lactic acid bacteria using the functional hydrated hyaluronic acid. The acid tolerance of quadruply coated lactic acid bacteria using the functional hydrated hyaluronic acid also exhibit a pattern similar to that of conventional quadruple coated lactic acid bacteria, and thus quadruply coated lactic acid bacteria using the functional hydrated hyaluronic acid can be expected to be structurally stable form.

<8-3> Bile Tolerance of Quadruply Coated Lactic Acid Bacteria Using the Functional Hydrated Hyaluronic Acid The survival rates of the functional hydrated hyaluronic acid and the quadruply coated lactic acid bacteria using the hyaluronic acid were compared in vitro when exposed to bile acids. The experiment was carried out in the same manner as in Example <6-3> of the present invention.

The results are shown in Table 14 below.

TABLE 14

Bile tolerance results of quadruply coated lactic acid bacteria using the functional hydrated hyaluronic acid

| Coating | Microorganism | MRS | MRS + 0.3% bile | Viability(%) |
|---|---|---|---|---|
| Quadruple coating using hyaluronic acid | Lactobacillus acidophilus IDCC 3302 | 245 | 206 | 84 |
| | Lactobacillus bulgaricus | 160 | 137 | 86 |
| | Lactobacillus casei | 180 | 153 | 85 |
| | Lactobacillus fermentum | 182 | 160 | 88 |
| | Lactobacillus gasseri | 168 | 146 | 87 |
| | Lactobacillus helveticus | 152 | 130 | 85 |
| | Lactobacillus johnsonii | 144 | 113 | 79 |
| | Lactobacillus paracasei | 152 | 118 | 78 |
| | Lactobacillus plantarum | 172 | 134 | 78 |
| | Lactobacillus reuteri | 210 | 165 | 79 |
| | Lactobacillus rhamnosus | 258 | 211 | 82 |
| | Lactobacillus salivarius | 190 | 161 | 85 |
| | Bifidobacterium bifidum | 243 | 194 | 80 |
| | Bifidobacterium breve | 255 | 188 | 74 |
| | Bifidobacterium lactis | 229 | 171 | 75 |
| | Bifidobacterium longum | 240 | 182 | 76 |
| | Enterococcus faecium | 260 | 187 | 72 |
| | Lactococcus lactis | 185 | 133 | 72 |
| | Streptococcus thermophilus | 151 | 111 | 74 |
| Quadruple coating using functional hydrated hyaluronic acid | Lactobacillus acidophilus IDCC 3302 | 235 | 185 | 79 |
| | Lactobacillus bulgaricus | 150 | 117 | 78 |
| | Lactobacillus casei | 170 | 130 | 77 |
| | Lactobacillus fermentum | 162 | 126 | 78 |
| | Lactobacillus gasseri | 178 | 137 | 77 |
| | Lactobacillus helveticus | 142 | 107 | 76 |
| | Lactobacillus johnsonii | 134 | 92 | 69 |
| | Lactobacillus paracasei | 142 | 102 | 72 |
| | Lactobacillus plantarum | 162 | 110 | 68 |
| | Lactobacillus reuteri | 193 | 127 | 66 |
| | Lactobacillus rhamnosus | 232 | 160 | 69 |
| | Lactobacillus salivarius | 172 | 113 | 66 |
| | Bifidobacterium bifidum | 224 | 150 | 67 |
| | Bifidobacterium breve | 215 | 141 | 66 |
| | Bifidobacterium lactis | 219 | 148 | 68 |
| | Bifidobacterium longum | 210 | 142 | 68 |
| | Enterococcus faecium | 220 | 151 | 69 |
| | Lactococcus lactis | 175 | 119 | 68 |
| | Streptococcus thermophilus | 131 | 83 | 64 |

As shown in Table 14 above, the bile tolerance of quadruply coated lactic acid bacteria using the functional hydrated hyaluronic acid and quadruply coated lactic acid bacteria using conventional hyaluronic acid was compared. Thus, it is considered that quadruply coated lactic acid bacteria using the functional hydrated hyaluronic acid maintain a structurally stable form because the bile tolerance in each experimental group was similar with almost no difference.

<8-4> Non-Competitive Adhesion of Quadruply Coated Lactic Acid Bacteria Using the Functional Hydrated Hyaluronic Acid The quadruply coated lactic acid bacteria were prepared on the basis of the quadruply coated lactic acid bacteria preparation method of Korean Patent No. 10-1280232 in order to compare the adhesion ability in the absence of competitive microorganisms. In addition, in order to evaluate the non-competitive adhesion, the same procedure as in Example <6-4> of the present invention was performed.

The results are shown in Table 15 below.

As shown in Table 15 below, the adhesion efficiency of quadruply coated lactic acid bacteria using hyaluronic acid was relatively better than that of uncoated lactic acid bacteria in the evaluation of adhesion capacity to Caco-2 cells similar to the intestinal membrane. The adhesion efficiency of quadruply coated lactic acid bacteria using the functional hydrated hyaluronic acid was equivalent to that of quadruply coated lactic acid bacteria using the hyaluronic acid.

TABLE 15

Non-competitive adhesion of quadruply coated lactic acid bacteria using the functional hydrated hyaluronic acid

| | Adhesion of lactic acid bacteria (%) | | |
|---|---|---|---|
| Classification | Un-coated | Hyaluronic acid quadruple coating | Functional hydrated hyaluronic acid quadruple coating |
| Lactobacillus acidophilus IDCC 3302 | 26 | 64 | 66 |
| Lactobacillus bulgaricus | 5 | 47 | 48 |
| Lactobacillus casei | 8 | 51 | 47 |
| Lactobacillus fermentum | 5 | 54 | 49 |
| Lactobacillus gasseri | 12 | 56 | 50 |
| Lactobacillus helveticus | 15 | 58 | 53 |
| Lactobacillus johnsonii | 35 | 67 | 63 |
| Lactobacillus paracasei | 17 | 53 | 49 |
| Lactobacillus plantarum | 15 | 59 | 55 |
| Lactobacillus reuteri | 8 | 45 | 42 |
| Lactobacillus rhamnosus | 34 | 72 | 68 |
| Lactobacillus salivarius | 5 | 44 | 42 |
| Bifidobacterium bifidum | 13 | 58 | 55 |

TABLE 15-continued

Non-competitive adhesion of quadruply coated lactic acid bacteria using the functional hydrated hyaluronic acid

| | Adhesion of lactic acid bacteria (%) | | |
|---|---|---|---|
| Classification | Un-coated | Hyaluronic acid quadruple coating | Functional hydrated hyaluronic acid quadruple coating |
| Bifidobacterium breve | 17 | 54 | 58 |
| Bifidobacterium lactis | 24 | 55 | 59 |
| Bifidobacterium longum | 23 | 53 | 55 |
| Enterococcus faecium | 38 | 69 | 66 |
| Lactococcus lactis | 32 | 65 | 62 |
| Streptococcus thermophilus | 14 | 56 | 53 |

It was confirmed that the adhesion ability of the quadruply coated lactic acid bacteria using the functional hydrated hyaluronic acid was further improved according to the number of coatings. In other words, when only the results of *Lactobacillus acidophilus* IDCC 3302 were evaluated, it was confirmed that dual coated lactic acid bacteria using the functional hydrated hyaluronic acid (48% adhesion rate), tertiary coated lactic acid bacteria using the functional hydrated hyaluronic acid (56% adhesion rate), and quadruply coated lactic acid bacteria using the functional hydrated hyaluronic acid (66% adhesion rate) increased adhesion rate by 20% or more according to the number of coatings. These results suggest that maltodextrin as the third coating agent and whey protein as the quaternary coating agent minimize the exposure of lactic acid bacteria to the acidic environment and that the second coating agent also maximizes the interaction with the mucosa by reducing the exposure time.

<8-5> Competitive Exclusion of Quadruply Coated Lactic Acid Bacteria Using the Functional Hydrated Hyaluronic Acid In order to more clearly determine whether quadruply coated lactic acid bacteria using the functional hydrated hyaluronic acid can exhibit beneficial physiological activity in the intestines, the present inventors were carried out in the same manner as in Example <6-5> of the present invention to evaluate the adherence ability of the lactic acid bacteria in the presence of resident flora.

The results are shown in Table 16 below.

As shown in Table 16 below, *Salmonella typhimurium* KCTC 2054, which is a harmful microorganism, was first attached to Caco-2 cells similar to intestinal membranes. The harmful bacteria are competitive with the uncoated, hyaluronic acid quadruple coating, and quadruply coated lactic acid bacteria using the functional hydrated hyaluronic acid. As a result of comparing the removal rates of the harmful bacteria, uncoated lactic acid bacteria that do not contain functional substances have relatively low removal efficiency because they remove *Salmonella typhimurium* KCTC 2054 by a competition removal method. The quadruply coated lactic acid bacteria using the functional hydrated hyaluronic acid showed significantly higher removal efficiency of the harmful bacteria than the uncoated and hyaluronic acid quadruple coated lactic acid bacteria.

Meanwhile, the effect of the quadruply coated lactic acid bacteria using the functional hydrated hyaluronic acid was 57% superior to that of the uncoated lactic acid bacteria, and the result of *Lactobacillus acidophilus* IDCC 3302, and it also showed an excellent effect of 31% or more even in comparison with the conventional hyaluronic acid quadruply coated lactic acid bacteria. Therefore, when the functional hydrated hyaluronic acid is used as coating agent for lactic acid bacteria, it has been found that the inhibitory effect against harmful bacteria in the intestines is remarkably improved as compared with conventional lactic acid bacteria coating agents.

TABLE 16

Competitive exclusion of quadruply coated lactic acid bacteria using the functional hydrated hyaluronic acid

| | Competitive exclusion of *Salmonella typhimurium* (%) | | |
|---|---|---|---|
| Classification | Un-coated | Hyaluronic acid quadruple coating | Functional hydrated hyaluronic acid quadruple coating |
| Lactobacillus acidophilus IDCC 3302 | 31 | 57 | 88 |
| Lactobacillus bulgaricus | 22 | 49 | 82 |
| Lactobacillus casei | 38 | 60 | 92 |
| Lactobacillus fermentum | 26 | 52 | 78 |
| Lactobacillus gasseri | 32 | 55 | 82 |
| Lactobacillus helveticus | 20 | 58 | 75 |
| Lactobacillus johnsonii | 27 | 69 | 91 |
| Lactobacillus paracasei | 21 | 58 | 82 |
| Lactobacillus plantarum | 24 | 48 | 69 |
| Lactobacillus reuteri | 23 | 59 | 78 |
| Lactobacillus rhamnosus | 33 | 59 | 88 |
| Lactobacillus salivarius | 11 | 47 | 72 |
| Bifidobacterium bifidum | 16 | 49 | 72 |
| Bifidobacterium breve | 15 | 47 | 65 |
| Bifidobacterium lactis | 18 | 48 | 78 |
| Bifidobacterium longum | 22 | 49 | 72 |
| Enterococcus faecium | 35 | 56 | 73 |
| Lactococcus lactis | 24 | 58 | 75 |
| Streptococcus thermophilus | 13 | 49 | 77 |

The competitive adhesion inhibition of quadruply coated lactic acid bacteria using the functional hydrated hyaluronic acid was improved to about 30% as compared with the simple adhesion ability evaluated in the above Example <8-4>. These results suggest that if the conventional quadruple coated lactic acid bacteria multiply by increasing the adhesion efficiency through competition exclusion, quadruply coated lactic acid bacteria using the functional hydrated hyaluronic acid was expected to increase the chance of adhesion by decreasing the activity of competing strain *Salmonella typhimurium* by combining competitive exclusion with antimicrobial activity.

<8-6> In Vivo Intestinal Fixation of Quadruply Coated Lactic Acid Bacteria Using the Functional Hydrated Hyaluronic Acid For the in vivo intestinal fixation test of quadruply coated lactic acid bacteria using the functional hydrated hyaluronic acid, the same experiment as in Example <6-6> of the present invention was performed.

Figure 10:
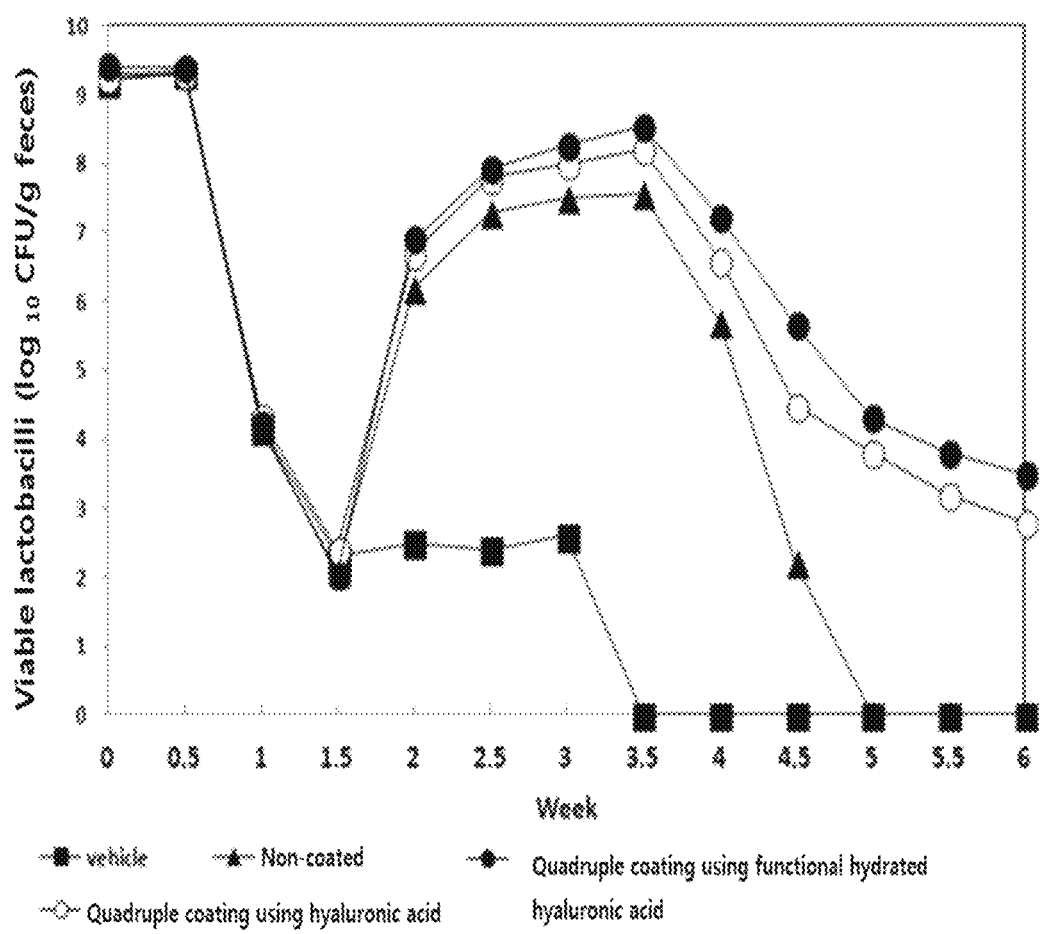
FIG. 10 is a diagram comparing intestinal fixation of quadruply coated *Lactobacillus acidophilus* IDCC 3302 using functional hydration hyaluronic acid, and quadruply coated *Lactobacillus acidophilus* IDCC 3302 using conventional hyaluronic acid and uncoated *Lactobacillus acidophilus* IDCC 3302.

The results are shown in FIG. 10.

As shown in FIG. 10, it was confirmed that *Lactobacillus* bacteria were detected in the feces up to 2.5 weeks after discontinuation of the treatment with quadruply coated lactic acid bacteria using hyaluronic acid and quadruply coated lactic acid bacteria using the functional hydrated hyaluronic acid compared with the uncoated lactic acid bacteria. The effect was confirmed to be the best in quadruply coated lactic acid bacteria using the functional hydrated hyaluronic acid.

On the other hand, *Lactobacillus* was detected in the feces for up to one week after discontinuation of the uncoated lactic acid bacteria, and it was confirmed that the best fixing performance was obtained since quadruply coated lactic acid bacteria using the functional hydrated hyaluronic acid group was detected by extending 1.5 weeks further.

<8-7> In Vivo Harmful Bacteria Inhibition of Quadruply Coated Lactic Acid Bacteria Using Functional Hydrated Hyaluronic Acid In order to confirm the inhibitory ability against harmful bacteria in quadruply coated lactic acid bacteria using the functional hydrated hyaluronic acid in vivo, the antimicrobial activity in the mouse model infected with *Salmonella typhimurium* KCTC 2054 was performed in the same manner as in Example <6-7> of the present invention.

Figure 11:
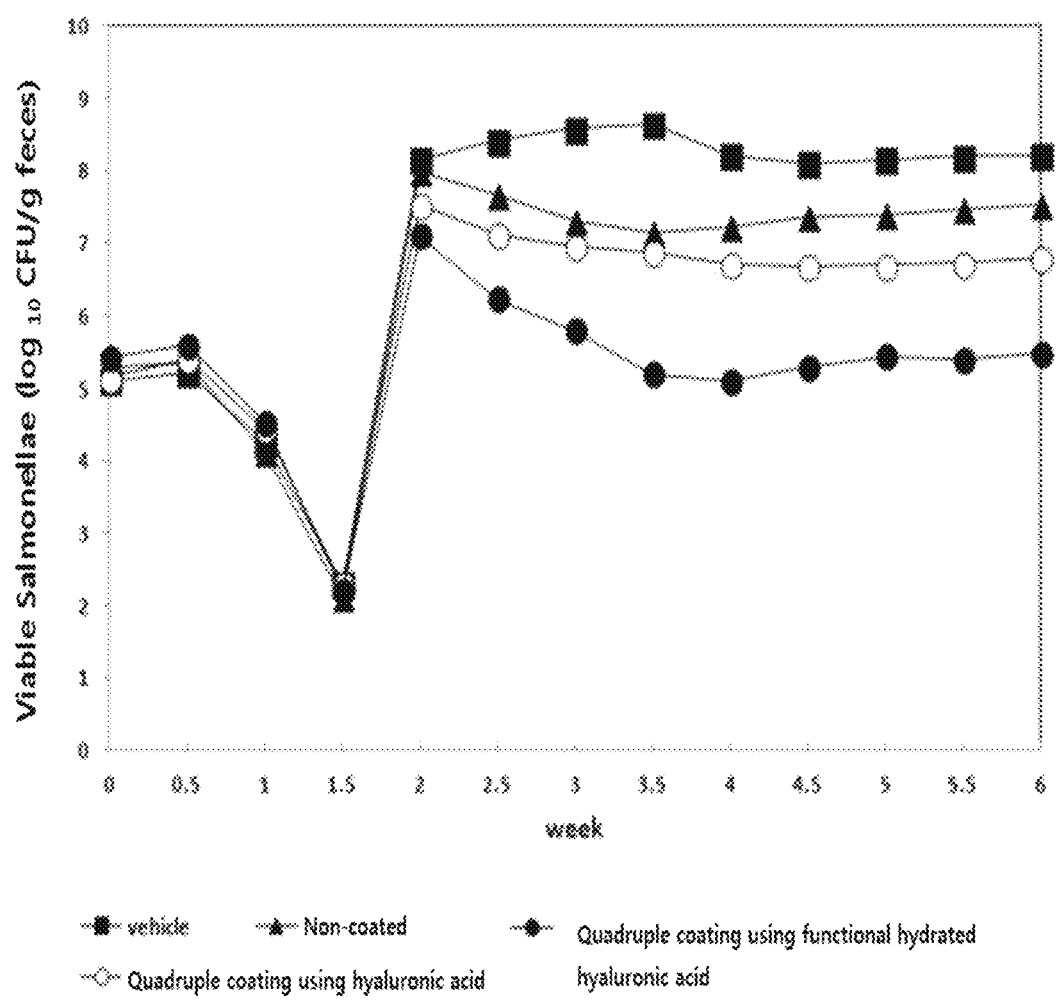
FIG. 11 is a diagram evaluating the effect of quadruply coated *Lactobacillus acidophilus* IDCC 3302 using the functional hydration hyaluronic acid, and quadruply coated *Lactobacillus acidophilus* IDCC 3302 using conventional hyaluronic acid and uncoated *Lactobacillus acidophilus* IDCC 3302 on the growth of intestinal *Salmonella*.
Figure 12:
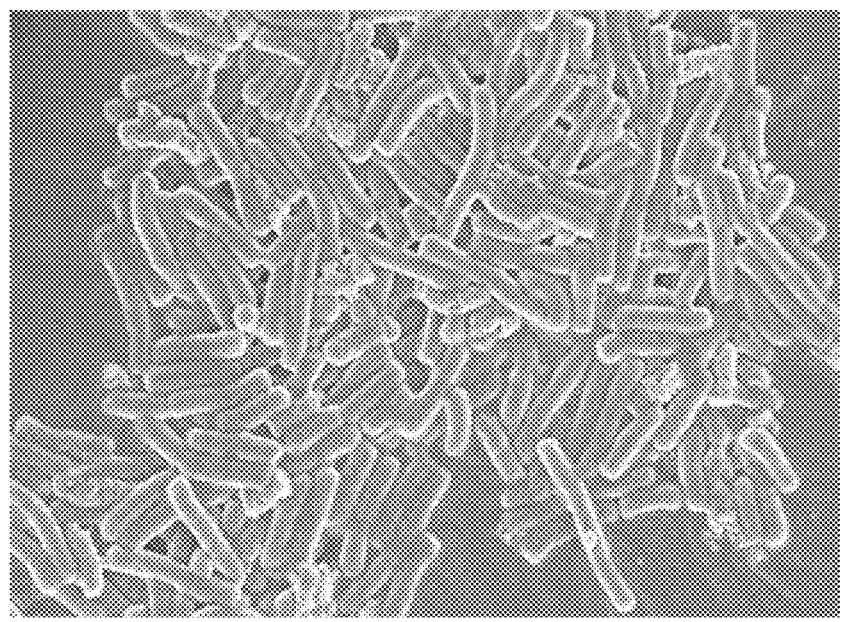
FIG. 12 is a SEM photograph showing the shape of the uncoated *Lactobacillus acidophilus* IDCC 3302 used in the present invention.

The results are shown in FIG. 11.

As shown in FIG. 11, as a result of administration of uncoated, quadruply coated lactic acid bacteria using the hyaluronic acid, and quadruply coated lactic acid bacteria using the functional hydrated hyaluronic acid to a mouse model which inhibited resident flora by antibiotics and was infected with *Salmonella typhimurium* KCTC 2054, it was found that the growth of the uncoated and quadruply coated lactic acid bacteria using hyaluronic acid, which plays a role of exclusion of simple competition, was inhibited by competing with *Salmonella typhimurium* KCTC 2054, but quadruply coated lactic acid bacteria using the functional hydrated hyaluronic acid inhibited *Salmonella typhimurium* KCTC 2054 more efficiently for a long time.

Meanwhile, quadruply coated lactic acid bacteria using the functional hydrated hyaluronic acid, which have both antimicrobial activity and competition exclusion, suppresses the growth from the beginning after infection with *Salmonella typhimurium* KCTC 2054, so that the influence of the harmful bacteria *Salmonella typhimurium* KCTC 2054 harmful bacteria less affected. Thus, because of the increased number of lactic acid bacteria by the proliferation of lactic acid bacteria, it helped to maintain the normal flora even after 2.5 weeks of discontinuation.

Example 9

Electron Microscope (FE-SEM) Structure Analysis

Structural analysis of quadruply coated *Lactobacillus acidophilus* IDCC 3302 using the functional hydrated hyaluronic acid prepared in Example 1 was carried out by electron microscopic photographing. The structure analysis of quadruply coated lactic acid bacteria using the functional hydrated hyaluronic acid were shown in FIGS. 12 to 16 by electron microscopic stepwise.

Figure 13:
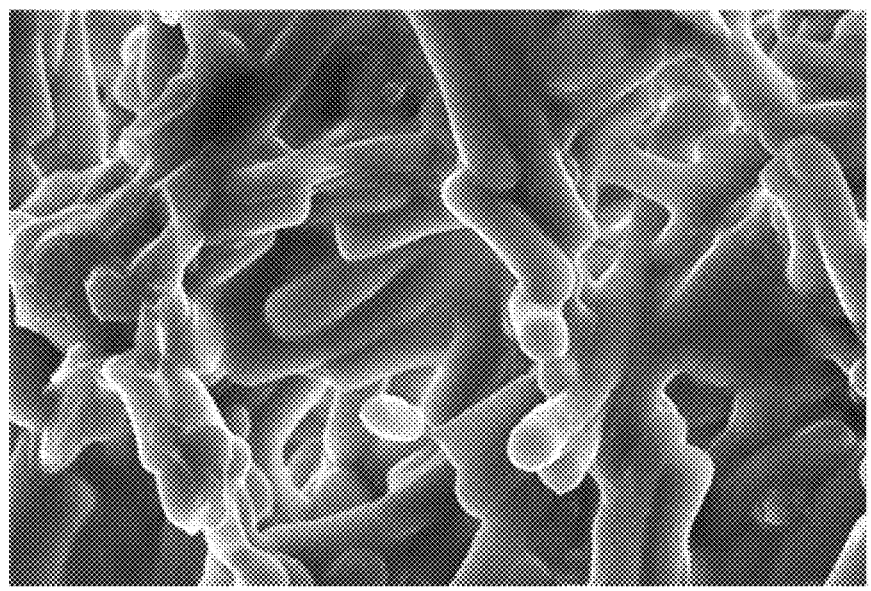
FIG. 13 is a SEM photograph showing the shape of the primary coated lactic acid bacteria mixed with *Lactobacillus acidophilus* IDCC 3302 and carboxymethyl cellulose.
Figure 14:
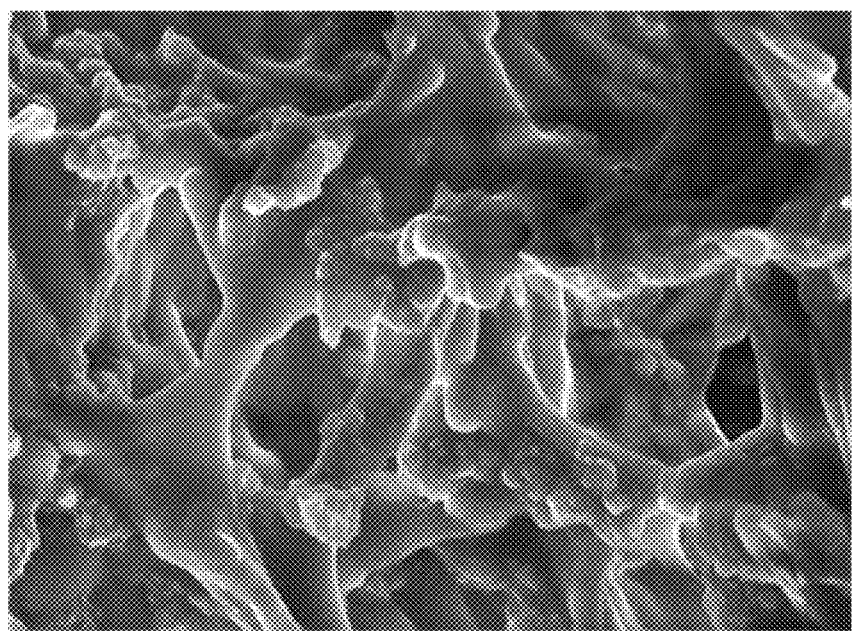
FIG. 14 is an SEM photograph showing the shape of secondary coated lactic acid bacteria mixed with functional hydrolyzed hyaluronic acid in *Lactobacillus acidophilus* IDCC 3302, which is primary coated with carboxymethylcellulose.
Figure 15:
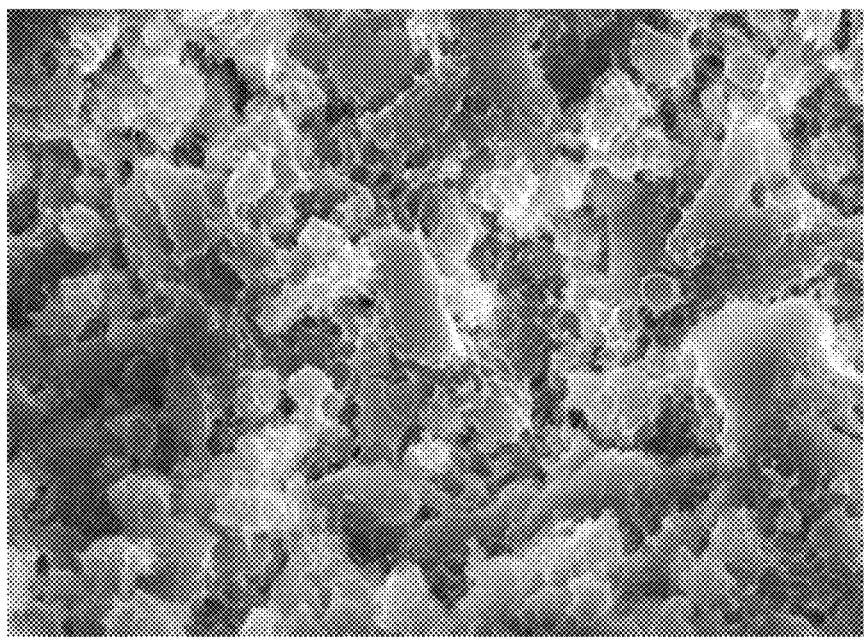
FIG. 15 is an SEM photograph showing the shape of tertiary coated lactic acid bacteria mixed with maltodextrin in *Lactobacillus acidophilus* IDCC 3302 secondary coated with carboxymethylcellulose and functional hydrated hyaluronic acid.
Figure 16:
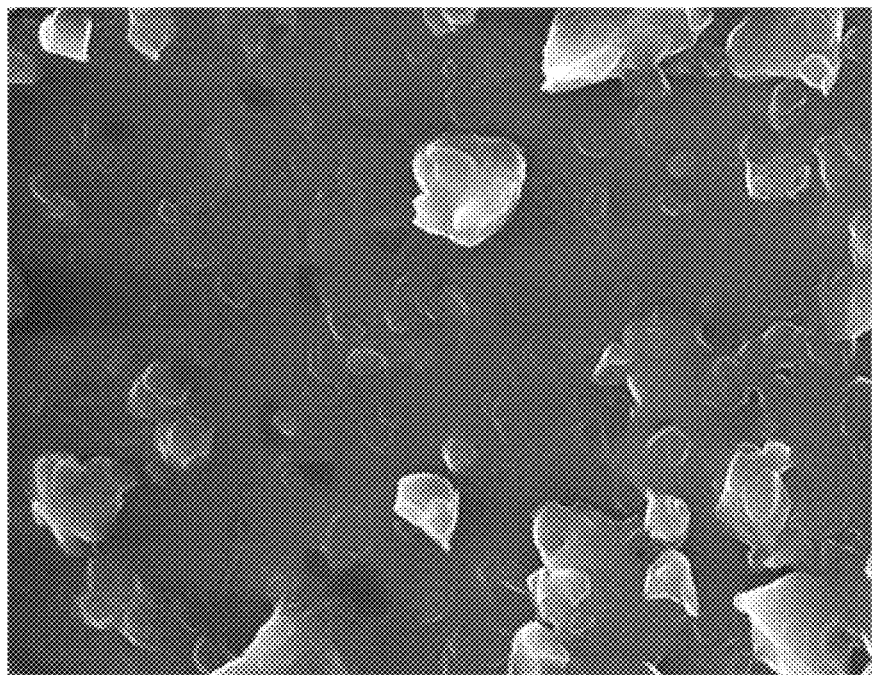
FIG. 16 is an SEM photograph showing the shape of quaternary coated lactic acid bacteria mixed with whey proteins in *Lactobacillus acidophilus* IDCC 3302, which is tertiary coated with carboxymethylcellulose, functional hydrated hyaluronic acid, and maltodextrin.

As shown in FIGS. 12 to 16, when CMC-Na was mixed with lactic acid bacteria, it was observed that the surface of the lactic acid bacteria was coated with CMC-Na as forming a film-like thin film (FIG. 13). In addition, it was observed that the structure of the functional hydrated hyaluronic acid structure became denser by mixing CMC-Na and the functional hydrated hyaluronic acid (FIG. 14). Maltodextrin, a porous particle, was added to prevent external moisture and temperature from being easily transferred to bacteria (FIG. 15). Finally, the cells were coated with whey protein and the cells were not exposed to the outside (FIG. 16).

Thus, as the first to fourth coatings were sequentially added, it was confirmed that the coating agents used with the lactic acid bacteria protected the lactic acid bacteria more densely and firmly.

INDUSTRIAL APPLICABILITY

The functional hydrated hyaluronic acid of the present invention has an effect of exhibiting a selective antagonism by exhibiting a proliferation inhibitory action against harmful bacteria and a proliferation promoting action for beneficial bacteria. The functional hydrated hyaluronic acid of the present invention can be used as quadruply coated lactic acid bacteria by mixing a lactic acid bacterium with a water-soluble polymer, a functional hydrated hyaluronic acid, a coating agent having porous particles and a protein. And thus, the functional hydrated hyaluronic acid not only exhibits excellent adhesion to the intestinal mucosa and selective antagonism against harmful bacteria which are not present in conventional uncoated, single, dual, tertiary and quadruple coated lactic acid bacteria, but also has excellent acid tolerance and bile tolerance. Therefore, the functional hydrated hyaluronic acid has an effect of not losing the physiological activity inherent in lactic acid bacteria, and thus is highly industrially applicable.

What is claimed is:

1. A method for preparing a quadruply coated lactic acid bacteria, the method comprising:
    (a) conducting a primary coating by mixing a water-soluble polymer with a lactic acid bacteria;
    (b) conducting a secondary coating by mixing a functional hydrated hyaluronic acid complexed with a fermented product of a lactic acid bacteria with the primarily coated lactic acid bacteria of step (a), wherein the fermented product of a lactic acid bacteria comprises an adhesion inhibitor of a harmful bacteria, wherein the adhesion inhibitor is selected from the croup consisting of lipoteichoic acid and peptidoglycan, and wherein the functional hydrated hyaluronic acid complexed with the fermented product of a lactic acid bacteria is prepared by a process comprising: adding hyaluronic acid to a tyndallized culture medium of a lactic acid bacteria in a ratio of 0.001 to 1 part by weight of hyaluronic acid to 100 parts by weight of a tyndallized culture medium of a lactic acid bacteria, and dissolving the hyaluronic acid in the culture medium of a lactic acid bacteria upon stirring, followed by concentration;
    (c) conducting a tertiary coating by mixing a coating agent having porous particles with the secondarily coated lactic acid bacteria of step (b); and
    (d) conducting a quaternary coating by mixing a protein with the tertiarily coated lactic acid bacteria of step (c).

2. The method of claim 1, wherein the water-soluble polymer in step (a) is at least one selected from the group consisting of carboxymethylcellulose (CMC), hydroxyethylcellulose (HEC), xanthan gum (XG), guar gum (GG), polyvinylpyrrolidone (PVP), carbopol, sodium alginate, and propylene glycol alginate.

3. The method of claim 1, wherein the concentration of step (b) is under a reduced pressure at 30 to 60° C.

4. The method of claim 1, wherein the coating agent having porous particles in step (c) is at least one selected from the group consisting of alginate, maltodextrin (MD), chitosan, starch, polyethylene glycol (PEG), triacetin, propylene glycol, acetyl triethyl citrate, triethyl citrate, and glycerin.

5. The method of claim 1, wherein the protein in step (d) is at least one selected from the group consisting of skim milk powder, whey protein, and isolated soybean protein.

6. The method of claim 1, wherein the lactic acid bacteria are at least one selected from the group consisting of *Lactobacillus* sp., *Bifidobacterium* sp., *Streptococcus* sp., *Lactococcus* sp., *Enterococcus* sp., *Pediococcus* sp., *Leuconostoc* sp., and *Weissella* sp.

7. The method of claim 1, wherein the method comprises
    (a) conducting the primary coating by mixing the water-soluble polymer with a culture medium of the lactic acid bacteria in a ratio of 0.1 to 10 parts by weight of the soluble polymer to 100 parts by weight of the culture medium of the lactic acid bacteria;

(b) conducting the secondary coating by mixing the functional hydrated hyaluronic acid with a tyndallized culture medium of the lactic acid bacteria in a ratio of 0.001 to 0.5 parts by weight of the functional hydrated hyaluronic acid to 100 parts by weight of the tyndallized culture medium of the lactic acid bacteria;

(c) conducting the tertiary coating by mixing the coating agent having the porous particles with a culture medium of the lactic acid bacteria in a ratio of 0.1 to 10 parts by weight of the coating agent to 100 parts by weight of the culture medium of the lactic acid bacteria; and (d) conducting the quaternary coating by mixing the protein with a culture medium of the lactic acid bacteria in a ratio of 1 to 30 parts by weight of the protein to 100 parts by weight of the culture medium of the lactic acid bacteria.

* * * * *